(12) United States Patent
Kuliopulos et al.

(10) Patent No.: US 6,864,229 B2
(45) Date of Patent: Mar. 8, 2005

(54) G PROTEIN COUPLED RECEPTOR (GPCR) AGONISTS AND ANTAGONISTS AND METHODS OF ACTIVATING AND INHIBITING GPCR USING THE SAME

(75) Inventors: Athan Kuliopulos, Winchester, MA (US); Lidija Covic, Boston, MA (US)

(73) Assignee: New England Medical Center Hospitals, Inc., Boston, MA (US)

( * ) Notice: Subject to any disclaimer, the term of this patent is extended or adjusted under 35 U.S.C. 154(b) by 268 days.

(21) Appl. No.: 09/841,091

(22) Filed: Apr. 23, 2001

(65) Prior Publication Data

US 2002/0076755 A1 Jun. 20, 2002

Related U.S. Application Data

(60) Provisional application No. 60/198,993, filed on Apr. 21, 2000.

(51) Int. Cl.[7] .............................. C07K 5/00; C07J 11/00; A61K 38/00; G01N 33/53
(52) U.S. Cl. ........................... 514/2; 530/350; 530/300; 552/540; 514/12; 435/7.1; 435/69.1
(58) Field of Search ................................ 530/350, 300; 435/69.1, 7.1, 320.1, 325; 514/12, 2; 552/540

(56) References Cited

U.S. PATENT DOCUMENTS

| | | |
|---|---|---|
| 5,747,267 A | 5/1998 | Mulvihill et al. |
| 5,925,549 A | 7/1999 | Hsueh et al. |
| 6,096,868 A | 8/2000 | Halsey et al. |
| 6,111,076 A | 8/2000 | Fukusumi et al. |
| 6,162,808 A | 12/2000 | Kindon et al. |

FOREIGN PATENT DOCUMENTS

| | | |
|---|---|---|
| WO | WO 98/00538 | 1/1998 |
| WO | WO 98/34948 | 8/1998 |
| WO | WO 99/43711 | 9/1999 |
| WO | WO 99/62494 | 12/1999 |

OTHER PUBLICATIONS

Coughlin, et al, 2003, J. Clin. Invest., 111(1): 25–27.*
Covic, et al. (2002). "Activation and inhibition of G protein–coupled receptors by cell–penetrating membrane–tethered peptides" *Proc Natl Acad Sci USA* 99(2): 643–648.
Covic, et al. (2000). "Intracellular liganding of the PAR1 thrombin receptor by a novel class of cell penetrating peptides" *Blood* 96(11): 244a. Abstract #1050.
Faruqi, et al. (2000). "Structure–Function Analysis of Protease–activated Receptor 4 Tethered Ligand Peptides" *J. Biol. Chem.* 275(26): 19728–19734.
Hammes and Coughlin (1999). "Protease–Activated Receptor–1 Can Mediate Responses to SFLLRN in Thrombin–Desensitized Cells: Evidence for a Novel Mechanism for Preventing or Terminating Signaling by PAR1's Tethered Ligand" *Biochem.* 38: 2486–2493.
Moro, et al. (1993). "Hydrophobic Amino Acid in the i2 Loop Plays a Key Role in Receptor–G Protein Coupling" *J. Biol. Chem.* 268(30): 22273–22276.
Swift, et al. (2000). "PAR1 Thrombin Receptor–G Protein Interactions" *J. Biol. Chem.* 275(4): 2627–2635.
Trejo and Coughlin (1999). "The Cytoplasmic Tails of Protease–activated Receptor–1 and Substance P Receptor Specify Sorting to Lysosomes versus Recycling" *J. Biol. Chem.* 274(4): 2216–2224.
International Search Report for PCT/US01/13063. Mailed on Apr. 9, 2002.
Elliot, J. T., Prestwich, G. D. (2000) Maleimide–Functionalized Lipids that Anchor Polypeptides to Lipid Bilayers and Membranes. *Bioconjugate Chemistry* 11(6):832–841.
Palczewski, K., Kumasaka, T., Hori, T., Behnke, C. A., Motoshima, H., Fox, B. A., Le Trong, I., Teller, D. C., Okada, T., Stenkamp, R. E., Yamamoto, M., Miyano, M. (2000) Crystal Structure of Rhodopsin: A G Protein–Coupled Receptor. *Science* 289:739–745.
Gether, U., Kobilka, B. K. (1998) G Protein–coupled Receptors. *J. Biol. Chemistry* 273:17979–17982.
Cotecchia, S., Ostrowski, J., Kjelsberg, M. A., Caron, M. G., Lefkowitz, R. J. (1992) Discrete Amino Acid Sequences of the $\alpha$1–Adrenergic Receptor Determine the Selectivity of Coupling to Phosphatidylinositol Hydrolysis. *J Biol. Chemistry* 267:1633–1639.
Kostenis E., Conklin, B. R., Wess, J. (1997) Molecular Basis of Receptor/G Protein Coupling Sensitivity Studies by Coexpression of Wild Type and Mutant m2 Muscarinic Receptors with Mutant $G\alpha_q$ Subunits. *Biochemistry* 36:1487–1495.
Kjelsberg, M. A., Cotecchia, S., Ostrowski, J., Caron, M. G., Lefkowitz, R. J. (1992) Constiutive Activator of the $\alpha_{1B}$–Adrenergic Receptor by All Amino Acid Substitutions at a Single Site. *J Biol. Chemistry* 267:1430–1433.
Luttrell, L. M., Ostrowski, J., Cotecchia, S., Kendall, H., Lefkowitz, R. J. (1993) Antagonism of Catecholamine Receptor Signaling by Expression of Cytoplasmic Domains of the Receptors. *Science* 259:1453–1457.
Okamoto T., Murayama, Y., Hayashi, Y., Inagaki, M., Ogata, E., Nishimoto, I. (1991) Identification of a $G_S$ Activator Region of the $\beta$2–Adrenergic Receptor That is Autoregulated via Protein Kinase A–Dependent Phosphorylation. *Cell* 67:723–730.
Gilman, A. G. (1987) G Proteins: Transducers of Receptor–Generated Signals. *Ann. Rev. Biochem.* 56:615–649.

(List continued on next page.)

*Primary Examiner*—Lorraine Spector
*Assistant Examiner*—Sandra Wegert
(74) *Attorney, Agent, or Firm*—Mintz, Levin, Cohn, Ferris, Glovsky and Popeo, P.C.; Ingrid A. Beattie; Nicholas P. Triano, III

(57) ABSTRACT

The invention relates generally to G protein coupled receptors and in particular to agonists and antagonists of G protein receptors and methods of using the same.

46 Claims, 20 Drawing Sheets

OTHER PUBLICATIONS

Higashijima, T., Uzu, S., Nakajima, T., Ross, E. M. (1988) Mastoparan, a Peptide Toxin from Wasp Venom, Mimics Receptors by Activating GTP–binding Regulatory Proteins (G Proteins). *J Biol. Chemistry* 263:6491–6494.

Bernatowicz, M. S., Klimas, C. E., Hartl, K. S., Peluso, M., Allegretto, N. J., Seiler, S. M. (1996) Development of Potent Thrombin Receptor Antagonist Peptides. *J. Med. Chem.* 39:4879–4887.

Kuliopulos, A., Covic, L., Seeley, S., Sheridan, P. J., Helin, J., Costello, C. E. (1999) Plasmin Desensitization of the PAR1 Thrombin Receptor: Kinetics, Sites of Truncation, and Implications for Thrombolytic Therapy. *Biochemistry* 38:4572–4585.

Rojas, M., Donahue, J. P., Tan, Z., Lin, Y. (1998) Genetic Engineering of Proteins with Cell Membrane Permeability. *Nature Biotechnology* 16:370–375.

Schwarze, S. R., Ho, A., Vocero–Akbani, A., Dowdy, S. F. (1999) In Vivo Protein Transduction: Delivery of a Biologically Active Protein into the Mouse. *Science* 285:1569–1572.

Wikstrom, P., Kirschke, H., Stone, S., Shaw, E. (1989) The Properties of Peptidyl Diazoethanes and Chloroethanes as Protease Inactivators. *Archives of Biochem. & Biophysics* 270:286–293.

Stephens, G., O'Luanaigh, N., Reilly, D., Harriott, P., Walker, B., Fitzgerald, D., Moran, N. (1998) A Sequence within the Cytoplasmic Tail of GpIIb Independently Activates Platlet Aggregation and Thromboxane Synthesis. *J Biol. Chemistry* 273:20317–20322.

Nystedt, S., Emilsson, K., Wahlestedt, C., Sundelin, J. (1994) Molecular Cloning of a Potential Proteinase Activated Receptor. *Proc. Natl. Acad. Sci.* 91:9208–9212.

Xu, W., Andersen, H., Whitmore, T. E., Presnell, S. R., Yee, D. P., Ching, A., Gilbert, T., Davie, E. W., Foster, D. C. (1998) Cloning and Characterization of Human Protease–Activated Receptor 4. *Proc. Natl. Acad. Sci.* 95:6642–6646.

Kahn, M. L., Zheng, Y., Huang, W., Bigornia, V., Zeng, D., Moff, S., Farese, R. V., Tam, C., Couglin, S. R. (1998) A Dual Thrombin Receptor System for Platelet Activation. *Nature* 394:690–694.

Covic, L., Gresser, A. L., Kuliopulos, A. (2000) Biphasic Kinetics of Activation and Signaling for PAR1 and PAR4 Thrombin Receptors in Platelets. *Biochemistry* 39:5458–5467.

Oosterom, J., Garner, K. M., den Dekker, W. K., Nijenhuis, W. A. J., Hendrick, Gispen, W. H., Burbach, J. P. H., Barsh, G. S., Adan, R. A. H. (2001) Common Structure for Melanocortin–4 Receptor Selectivity of Structurally Unrelated Melanocortin Agonist and Endogenous Antagonist, Agouti Protein. *J Biol. Chemistry* 276:931–936.

Milligan, G. (2000) Receptors as Kissing Cousins. *Science* 288:65–67.

Pfeiffer, M., Koch, T., Schröder, Klutzny, M., Kirscht, S., Kreienkamp, H., Höllt, V., Schulz, S. (2001) Homo– and Heterodimerization of Somatostatin Receptor Subtypes. *J Biol. Chemistry* 276:14027–14036.

Ishii et al. (1994). *J. Biol. Chem.* 269:1125–1130.

Tarasova, Nadya (1999). "Inhibition of G–Protein–coupled Receptor Function by Disruption of Transmembrane Domain Interactions" *J. Biol. Chem.* 274:34911–34915.

Vergnolle, et al. "Protease–Activated Receptors in Inflammation, Neuronal Signaling and Pain" *TRENDS Pharma. Sci.* 22:146–152.

Andrade–Gordon, et al., "Design, Synthesis, and Biological Characterization of a Peptide–Mimetic Antagonist for a Tethered–Ligand Receptor", *Proc. Natl. Acad. Sci. USA,* 96(22):12257–12262 (1999).

George, et al., "A Transmembrane Domain–Derived Peptide Inhibits DI Dopamine Receptor Function without Affecting Receptor Oligomerization", *J. Biol. Chem.,* 273(46):30244–30248 (1998).

Ishii, et al., "Determinants of Thrombin Receptor Cleavage", *J. Biol. Chem.,* 270(27):16435–16440 (1995).

* cited by examiner i3 LOOP

```
PAR1   RCLSSSAVANRS------------------------------------------------------------KKGRALF (SEQ ID NO: 1)
PAR2   RMLRSSAMDENS------------------------------------------------------------EKQRQRAIK (SEQ ID NO: 7)
CCK8   RELYLGLRFDGDSDSDSQSRVRNQGGLPGAVHQNGRCRPETGAVG--EDSDGCYVQLPRSRPALELTALTAPGPGSGSR----PTQAKLLAKGRVVR (SEQ ID NO: 19)
CCKA   LELYQGIKFEASQKKSAKER-----------------------------KPSTTSSGKYEDSDGCYLQKTRPPRKLERQLSTGSSRANRIRSNSSAANLMAKQRVIR (SEQ ID NO: 20)
Sub P  ITLWASEIPGDS------------------------------------------------------------SDRYHEQVSAKRKVVK (SEQ ID NO: 21)
SSTR2  KVKSSG----------------------------------------------------------------IRVGSSKRKKSEKKVTR (SEQ ID NO: 22)
PAR4   HTLAASG---------------------------------------------------------------RRYGHALR (SEQ ID NO: 9)
```

Fig. 6A

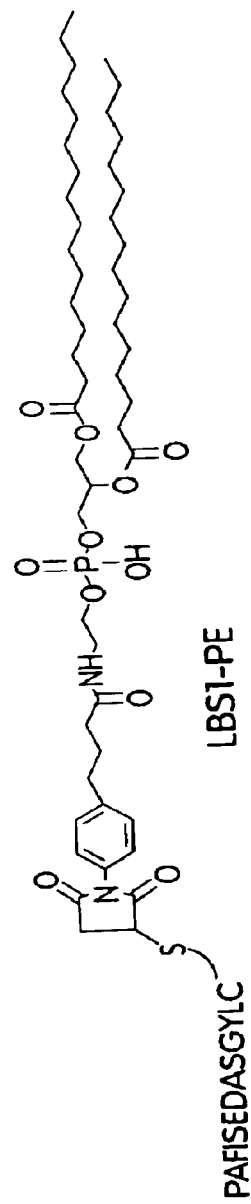
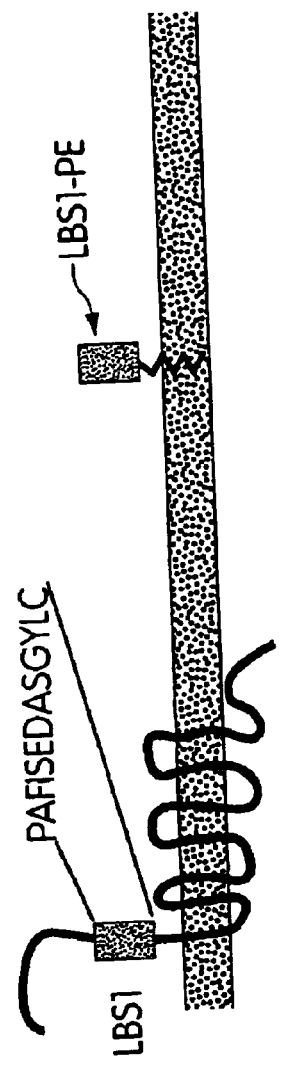
Fig. 9A
Fig. 9B

G PROTEIN COUPLED RECEPTOR (GPCR) AGONISTS AND ANTAGONISTS AND METHODS OF ACTIVATING AND INHIBITING GPCR USING THE SAME

RELATED APPLICATIONS

This application is related to U.S. Provisional Application No. 60/198,993, filed on Apr. 21, 2000, now abandoned the entire contents of which is incorporated herein by reference.

STATEMENT AS TO FEDERALLY SPONSORED RESEARCH

This invention was made with U.S. Government support under National Institutes of Health grants R01HL64701 and R01HL57905. The government has certain rights in the invention.

FIELD OF THE INVENTION

The invention relates generally to G protein coupled receptors and in particular to agonists and antagonists of G protein receptors and methods of using the same.

BACKGROUND OF THE INVENTION

A variety of hormones, neurotransmitters and biologically active substances control, regulate or adjust the functions of living bodies via specific receptors located in cell membranes. Many of these receptors mediate the transmission of intracellular signals by activating guanine nucleotide-binding proteins (hereinafter, sometimes referred to as G proteins) to which the receptor is coupled. Such receptors are generically referred to as G protein coupled receptors.

G protein coupled receptors (hereinafter sometimes termed "GPCR"s) comprise a large superfamily of receptors typically sharing a common structural motif of seven transmembrane helical domains. Some GPCRs do not have seven transmembrane helical domains and instead can be single-spanning transmembrane receptors for cytokines such as erythropoeitin, EGF, insulin, insulin-like growth factors I and II, TGF, or potentially multi-polypeptide receptors such as GPIb-V-IX or the collagen receptor that exhibit outside-in-signaling via G proteins. GPCRs play a vital role in the signaling processes that control cellular metabolism, cell growth and motility, inflammation, neuronal signaling, and blood coagulation. G protein coupled receptor proteins also have a very important role as targets for molecules such as hormones, neurotransmitters and physiologically active substances, which molecules control, regulate or adjust the functions of living bodies. For instance, GPCRs include receptors for biogenic amines, e.g., dopamine, epinephrine, histamine, glutamate (metabotropic effect), acetylcholine (muscarinic effect), and serotonin; for lipid mediators of inflammation such as prostaglandins, platelet activating factor, and leukotrienes; for peptide hormones such as calcitonin, C5a anaphylatoxin, follicle stimulating hormone, gonadotropin releasing hormone, neurokinin, oxytocin, and for proteases such as thrombin, trypsin, and factor VIIa/Xa; and for sensory signal mediators, e.g., retinal photopigments and olfactory stimulatory molecules. Each molecule has its own receptor protein which is specific thereto, whereby the specificities of individual physiologically active substances, including specific target cells and organs, specific pharmacological actions, specific action strength, action time, etc., are decided. Thus, GPCRs are a major target for drug action and development.

Although hundreds of G protein coupled receptor genes or cDNAs have been cloned, it is believed that there are still many uncharacterized G protein coupled receptors which have not been recognized as GPCRs, as of yet. GPCRs that lack known agonists are known as orphan receptors. Furthermore, there are currently no effective strategies to directly study the mechanism of receptor-G protein coupling in a controlled fashion under in vivo conditions. Nor is there an understanding of the selective contacts between receptors and G proteins, or the elucidation of the mechanisms of G protein activation by receptors.

Thus, a need remains in the art for compositions useful in defining a strategy that can be used to elucidate and further define selective contact site(s) between receptors and G proteins on the intracellular surface of the cell membrane, as well as a general molecular strategy for use in the facile development and screening of novel therapeutics targeted to receptor-effector interfaces.

SUMMARY OF THE INVENTION

The present invention is based on the discovery that the attachment of a hydrophobic moiety to peptides derived from the third intracellular loop of protease-activated receptor-1 (PAR1), PAR2, and PAR4, yields full agonists and/or antagonists of receptor-G protein signaling. These modified peptides—termed pepducins—exhibit excellent selectivity for their cognate receptor. In addition, pepducins for CCKB, CCKA, SSTR2 and MC4 are partial agonists and/or antagonists for their own receptors. Lipidated extracellular loop peptides were found to be full antagonists of extracellular ligands for PAR 1. Therefore, these novel molecular reagents will be applicable to a broad range of both known and unknown GPCRs.

One aspect of the present invention is directed to chimeric polypeptides. These polypeptides have a first domain that are either extracellular or intracellular portions of a G protein coupled receptor (GPCR), and at least a second domain, attached to the first domain. The second domain is a hydrophobic moiety which is either naturally or non-naturally occurring. Furthermore, the first domain does not comprise a native extracellular ligand of said GPCR.

In one embodiment, the second domain can be attached at one end or at an internal position of the first domain. If there are both a second and a third domain, they can be attached, interchangably, at both ends, or at internal positions within said first domain.

In a preferred embodiment the hydrophobic moiety is either a lipid moiety or an amino acid moiety. Equally preferrably, the hydrophobic moiety is selected from the group consisting of: phospholipids, steroids, sphingosines, ceramides, octyl-glycine, 2-cyclohexylalanine, benzolylphenylalanine, propionoyl ($C_3$); butanoyl ($C_4$); pentanoyl ($C_5$); caproyl ($C_6$); heptanoyl ($C_7$); capryloyl ($C_8$); nonanoyl ($C_9$); capryl ($C_{10}$); undecanoyl ($C_{11}$); lauroyl ($C_{12}$); tridecanoyl ($C_{13}$); myristoyl ($C_{14}$); pentadecanoyl ($C_{15}$); palmitoyl ($C_{16}$); phtanoyl (($CH_3$)$_4$); heptadecanoyl ($C_{17}$); stearoyl ($C_{18}$); nonadecanoyl ($C_{19}$); arachidoyl ($C_{20}$); heniecosanoyl ($C_{21}$); behenoyl ($C_{22}$); trucisanoyl ($C_{23}$); and lignoceroyl ($C_{24}$); wherein said hydrophobic moiety is attached to said chimeric polypeptide with amide bonds, sulfhydryls, amines, alcohols, phenolic groups, or carbon-carbon bonds. Equally, the hydrophobic moiety is either transmembrane domain 5 of the GPCR or a fragment thereof or a palmitate moiety.

In another embodiment, the extracellular portion is selected from the group consisting of: the first extracellular domain or a fragment thereof, the second extracellular loop or a fragment thereof, the third extracellular loop or a fragment thereof, and the fourth extracellular loop or a fragment thereof, of said G-protein coupled receptor.

In yet another embodiment, the intracellular portions is selected from the group consisting of: the first intracellular loop or a fragment thereof, the second intracellular loop or a fragment thereof, the third intracellular loop or a fragment thereof, and the fourth intracellular domain or a fragment thereof, of said G-protein coupled receptor. Preferrably, the intracellular portion is selected from the group consisting of: an intracellular domain of a one-transmembrane domain G-protein coupled receptor of the cytokine GPCR, or a fragment thereof, or an intracellular domain of a multi-polypeptide-GPCRs, such as a GPIb/V/IX receptor or a collagen receptor.

In one aspect, the extracellular or intracellular portion of the GPCR is at least 3 contiguous amino acid residues, and more preferrably, at least 5 contiguous amino acid residues.

In a preferred embodiment, the intracellular portion comprises the third intracellular loop of the GPCR. In a more preferred embodiment, the intracellular portion is at least 7 contiguous amino acid residues of the third intracellular loop. Specifically, it is preferred that the intracellualr portion is at least 7, preferably 14, amino acid residues of a GPCR transmembrane domain such as TM5 or a fragment thereof.

The G-protein coupled receptor or fragment thereof can be selected from any known or unknown GPCR, including, but not limited to a luteinizing hormone receptor, a follicle stimulating hormone receptor, a thyroid stimulating hormone receptor, a calcitonin receptor, a glucagon receptor, a glucagon-like peptide 1 receptor (GLP-1), a metabotropic glutamate receptor, a parathyroid hormone receptor, a vasoactive intestinal peptide receptor, a secretin receptor, a growth hormone releasing factor (GRF) receptor, protease-activated receptors (PARs), cholecystokinin receptors, somatostatin receptors, melanocortin receptors, ADP receptors, adenosine receptors, thromboxane receptors, platelet activating factor receptor, adrenergic receptors, 5-HT receptors, CXCR4, CCR5, chemokine receptors, neuropeptide receptors, opioid receptors, erythropoietin receptor, von Willebrand receptor, parathyroid hormone (PTH) receptor, vasoactive intestinal peptide (VIP) receptor, and collagen receptors.

In another aspect, the present invention is directed to the nucleic acids encoding a polypeptide of claim 1. These nucleic acids can then be introduced into a recombinant vector, which can then be used to transform any type of host cell.

The present invention also embodies methods of producing any of the peptides according to the present invention by cultivating a host cell as described under conditions sufficient to express the receptor.

In yet another aspect, the present invention includes methods for identifying a potential therapeutic agent for use in treatment of a pathology, wherein the pathology is related to aberrant expression or aberrant physiological interactions of a GPCR. The method comprises providing a cell having a GPCR or a property or function ascribable to said GPCR, contacting the cell with a composition comprising a candidate substance, contacting the cell with a composition comprising the chimeric polypeptide of claim 1, and determining whether the composition comprising the candidate substance alters the property or function ascribable to said GPCR. Thus, if an alteration observed in the presence of the substance is not observed when the cell is contacted with a composition devoid of the substance, the substance is identified as a potential therapeutic agent.

The present invention also includes methods of treating or preventing a pathology associated with a GPCR, wherein a polypeptide of the invention is administered to a subject in which such treatment or prevention is desired in an amount sufficient to treat or prevent said pathology in said subject. Preferrably, the subject is a human. The present invention also includes pharmaceutical compositions containing any of the polypeptides and/or nucleic acids of the invention and a pharmaceutically acceptable carrier. The invention also includes kits containing the pharmaceutical compositions.

Accordingly, the invention also includes methods for screening for a modulator of activity of a GPCR. The method comprises the steps of administering a test compound to a first test animal, wherein said first test animal expresses a desired GPCR, administering a polypeptide of claim 1 to a second test animal, measuring the activity of said test compound in said first test animal and said polypeptide in said second test animal, and comparing the activity of said polypeptide in said second test animal with the activity of said test compound in said first test animal with the activity of the desired GPCR in a control animal not administered said polypeptide. Thus, a change in the activity of said polypeptide in said first test animal relative to both said second test animal and said control animal indicates the test compound is a modulator of, an agonist of or an antagonist of said GPCR.

The invention further includes methods of treating a pathological state in a mammal through the administration of any polypeptide or nucleic acid of the invention.

Other features and advantages of the invention will be apparent from the following detailed description and claims.

BRIEF DESCRIPTION OF THE DRAWINGS

In FIG. 1A, the topological arrangement of the membrane-spanning segments (TM1–7), extracellular loops (e1–e4), and intracellular loops (i1–i4) of PAR1 is based on the X-ray structure of rhodopsin (K. Palczewski et al., *Science* 289, 739–45 (2000)) and is illustrated on the left. Thrombin cleaves the extracellular domain (e1) at the R41-S42 bond creating a new N-terminus, S42FLLRN, which functions as a tethered PAR1 agonist.

FIGS. 6A through 6D shows the fall specificity profiles of the PAR1 pepducins tested with six other GPCRs.

FIGS. 9A through 9E shows that LBS1-pepducin inhibits activation of PAR1.

DETAILED DESCRIPTION OF THE INVENTION

The present invention is based in part on the idea of selectively targeting the intracellular receptor-G-protein interface using cell-penetrating, membrane-tethered peptides. These peptides are tethered to the membrane through the attachment of a hydrophobic moiety to a G protein receptor or a fragment thereof. These modified peptides—termed pepducins—require the presence of their cognate receptor for activity and are highly selective for receptor type. This is the first report of intracellular reagents that exhibit receptor-specific and receptor-dependent effects on G protein signaling.

G Protein Coupled Receptors

The family of G protein-coupled receptors (GPCRs) has at least 250 members (Strader et al. FASEB J., 9:745–754, 1995; Strader et al. Annu. Rev. Biochem., 63:101–32, 1994). It has been estimated that one percent of human genes may encode GPCRs. GPCRs bind to a wide-variety of ligands ranging from photons, small biogenic amines (i.e., epinephrine and histamine), peptides (i.e., IL-8), to large glycoprotein hormones (i.e., parathyroid hormone). Upon ligand binding, GPCRs regulate intracellular signaling pathways by activating guanine nucleotide-binding proteins (G proteins). Interestingly, GPCRs have functional homologues in human cytomegalovirus and herpesvirus, suggesting that GPCRs may have been acquired during evolution for viral pathogenesis (Strader et al., FASEB J., 9:745–754, 1995; Arvanitakis et al. Nature, 385:347–350, 1997; Murphy, Annu. Rev. Immunol. 12:593–633, 1994).

Figure 1A:
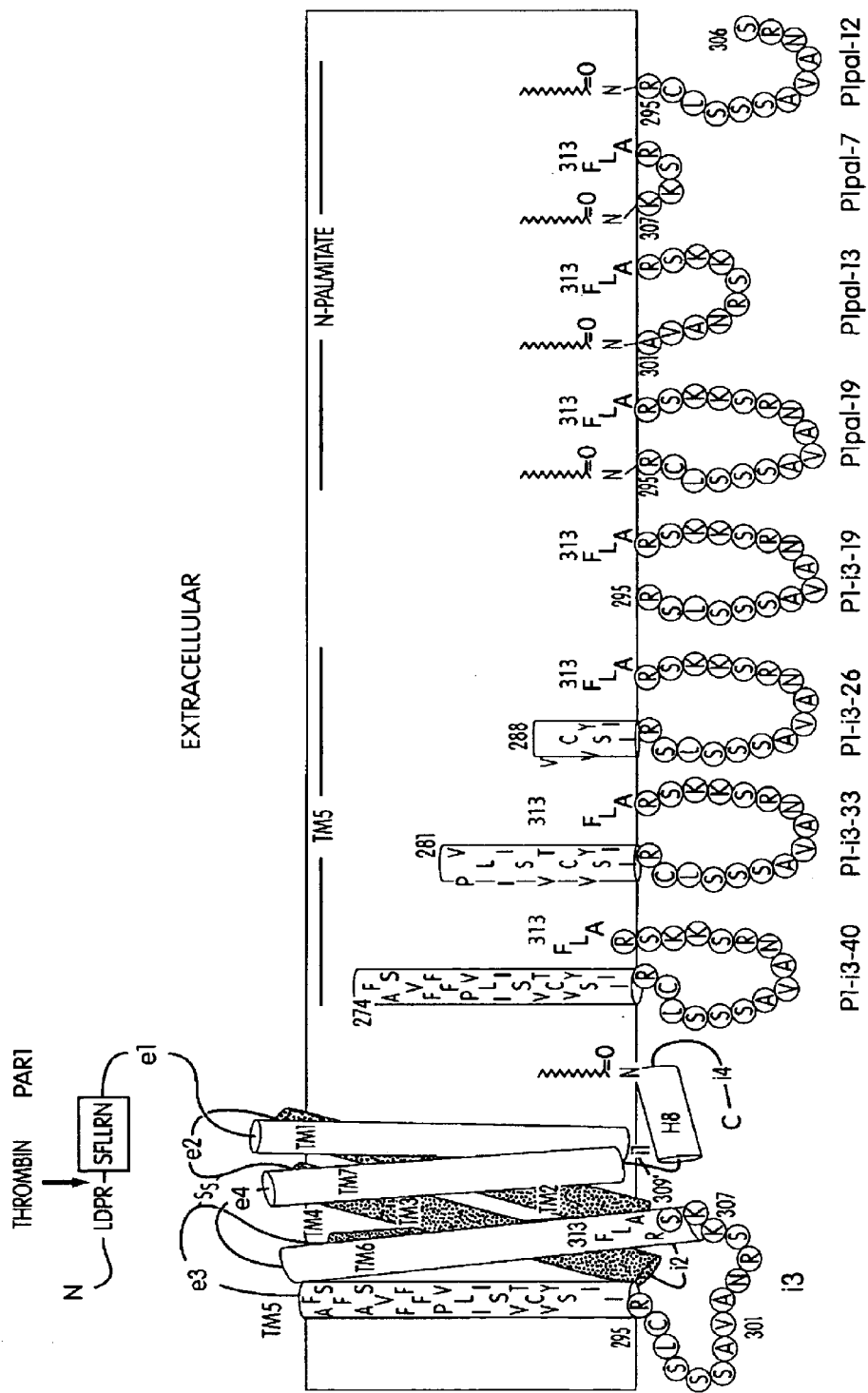
FIGS. 1A through 1E depict the schematic structure of the PAR1 receptor; membrane-tethered PAR1 i3-loop peptides of the present invention and their effect on the activation and/or regulation of Ca2+ signaling and aggregation in platelets.

The characteristic feature of most GPCRs which have been known up to now is that seven clusters of hydrophobic amino acid residues are located in the primary structure and pass through (span) the cell membrane at each region thereof (FIG. 1A). The domains are believed to represent transmembrane alpha-helices connected by three intracellular loops, three extracellular loops, and amino- and carboxyl-terminal domains (K. Palczewski et al., Science 289, 739–45 (2000)). Most GPCRs have single conserved cysteine residues in each of the first two extracellular loops which form disulfide bonds that are believed to stabilize functional protein structure. The 7 transmembrane regions are designated as TM1, TM2, TM3, TM4, TM5, TM6, and TM7. It is well known that these structures detailed above are common among G protein coupled receptor proteins and that the amino acid sequences corresponding to the area where the protein passes through the membrane (membrane-spanning region or transmembrane region) and the amino acid sequences near the membrane-spanning region are often highly conserved among the receptors. Thus, due to the high degree of homology in GPCRs, the identification of novel GPCRs, as well identification of both the intracellular and the extracellular portions of such novel members, is readily accomplished by those of skill in the art. By way of example, the book of Watson and Arkinstall (1994), incorporated herein by reference, provides the sequences of over 50 GPCRs. The book further describes, for each sequence, the precise residues comprising each of the transmembrane domains.

The binding sites for small ligands of G-protein coupled receptors are believed to comprise a hydrophilic socket located near the extracellular surface and formed by several G-protein coupled receptors transmembrane domains, which socket is surrounded by hydrophobic residues of the G-protein coupled receptors. The hydrophilic side of each G-protein coupled receptor transmembrane helix is postulated to face inward and form the polar ligand binding site. TM3 has been implicated in several G-protein coupled receptors as having a ligand binding site, such as including the TM3 aspartate residue. Additionally, TM5 serines, a TM6 asparagine and TM6 or TM7 phenylalanines or tyrosines are also implicated in ligand binding. The ligand binding site for peptide hormones receptors and receptors with other larger ligands such as glycoproteins (LH, FSH, hCG,TSH), and the Ca2+/glutamate/GABA classes of receptors likely residue in the extracellular domains and loops.

A key event for the switch from inactive to active receptor is ligand-induced conformational changes of transmembrane helices 3 (TM3) and 6 (TM6) of the GPCRs that have 7 transmembrane spanning helices (U. Gether, and B. K. Kolbilka, *J. Biol. Chem.* 273, 17979–17982 (1998)). These helical movements in turn alter the conformation of the intracellular loops of the receptor to promote activation of associated heterotrimeric G proteins. Mutagenesis studies (S. Cotecchia, J. Ostrowski, M. A. Kjelsberg, M. G. Caron and R. J. Lefkowitz, *J. Biol. Chem.* 267, 1633–1639 (1992); E. Kostenis, B. R. Conklin and J. Wess, *Biochemistry* 36, 1487–1495 (1997); M. A. Kjelsberg, S. Coteechia, J. Ostrowski, M. G. Caron, and R. J. Lefkowitz, *J. Biol. Chem.* 267, 1430–1433 (1992)) demonstrated that the third intracellular loop (i3) mediates a large part of the coupling between receptor and G protein. I3 loops expressed as minigenes have also been shown to directly compete with adrenergic receptors for Gq binding (L. M. Luttrell, J. Ostrowski, S. Cotecchia, H. Kendal and R. J. Lefkowitz, *Science* 259, 1453–1457 (1993)), or can activate G proteins as soluble peptides in cell-free conditions ( T. Okamoto et al., *Cell* 67, 723–730 (1991)).

Advantages of the Invention

The pepducin approach, according to the present invention, will allow the rich diversity of intracellular receptor structures to be exploited both for generation of new therapeutic agents and for delineation of the mechanisms of receptor-G protein coupling under in vivo conditions. This strategy may also prove to be more selective to the extent that the pepducins primarily target the receptor rather than the G protein. In addition, many receptors have been identified by genomic and genetic approaches as being important in various diseases processes but have no known ligands—so-called orphan receptors. One could potentially develop pepducin agonists and antagonists tailored to these receptors and determine which signaling pathways are activated by the orphan receptor in the context of its native environment. Thus, in this post-genomic era, the pepducin approach may be widely applicable to the targeting of membrane proteins and may open up new experimental avenues in systems previously not amenable to traditional molecular techniques.

Overview of the Invention

The present invention is based on the creation of i3 loop peptides (FIG. 1A) with N-terminal hydrophobic transmembrane residues that would partition the peptides into and across the lipid bilayer of whole cells. The hydrophobic residues would also serve to anchor the peptide in the lipid bilayer and increase the effective molarity for potential targets such as the receptor-G protein interface. If properly bound, the exogenous i3 peptide would then disrupt receptor-G protein interactions and cause activation and/or inhibition of signaling. Thus, the methods and compositions, as well as the experiments detailed herein, demonstrate that selectively targeting the intracellular receptor-G-protein interface using cell-penetrating, membrane-tethered peptides results in agonists or antagonists of G-protein receptor signalling. Specifically, the attachment of a hydrophobic moiety, such as a palmitate group, to peptides derived from the third intracellular loop of protease-activated receptor-1 (PAR1), PAR2, and PAR4, yields full agonists and/or antagonists of G-protein receptor signaling.

Furthermore, to explain the ability of the pepducins to both activate and inhibit receptor-G protein signaling, a two-site mechanism has been proposed (FIG. 4E) which accommodates the biphasic activation and inhibition of the agonists and the inhibition of the antagonists. Pepducins, by virtue of their lipid tether, rapidly transduce the plasma membrane and achieve high effective molarity at the perimembranous interface. The pepducin agonist first occupies a high-affinity site at the intracellular surface of the GPCR. The bound agonist either stabilizes or induces the activated state of the receptor to turn on the associated G protein(s). After this first site becomes saturated, higher concentrations of pepducin begin to occupy a second, lower-affinity, inhibitory site that blocks signal transference to G protein in a dominant manner, perhaps by mimicking receptor i3-loop ground-state interactions with the G protein. The inhibition by the pepducin antagonists is coincident with the inhibitory phase of the agonists, thus the antagonists may also bind at this lower affinity site. Exogenous activation or inhibition of receptors by pepducins could reflect a potential dimerization mode whereby one receptor donates its intracellular loops to an adjacent receptor. There are several examples of receptor dimers that give rise to distinct signaling properties (G. Milligan, *Science* 288, 65–67 (2000). including the cytokine/GPCRs such as the EPO receptor (Guillard et al., *J. Biol. Chem.* (2001) 276, 2007–2013), however, the mechanism(s) of cross-receptor modulation is unknown.

The Pepducins of the Invention

Seven GPCRs were tested (PAR1, PAR2, PAR4, CCKA, CCKB, SSTR2, MC4) for their ability to be activated or inhibited by their cognate pepducin. We were able to demonstrate full antagonist activity for PAR1, PAR2 (FIG. 4D), PAR4 (FIGS. 4C–D), and SSTR2 'wild-type' pepducins with their cognate receptors with IC50 values of 1 to 3 micromolar as summarized in Table 1. Of these GPCRs, we first focused on the newly-discovered PAR4 (Kahn et. al., (1998) *Nature* 394, 690; Xu et al., (1998) *PNAS* 95, 6642) due to our own interest in developing reagents suitable for exploring the unique ability of PAR4 to cause prolonged Ca2+ transients and irreversible platelet aggregation (Covic et al., (2000) *Biochemistry* 39, 5458). To date, the best extracellular ligands to PAR4 bind with millimolar or high-micromolar affinity and PAR4 inhibitors have not been reported. In FIG. 4 we show that the anti-PAR4 pepducin, P4pal-15, inhibits PAR4 and not PAR1, whereas the converse is true for the anti-PAR1 pepducin, P1pal-12. Thus, P4pal-15 is the first described high-potency anti-PAR4 compound (IC50=0.6 micromolar in platelets) and is currently being used to help delineate the role of PAR4 in the vascular biology of mice (Covic, Misra, and Kuliopulos, unpublished data).

Figure 2A:
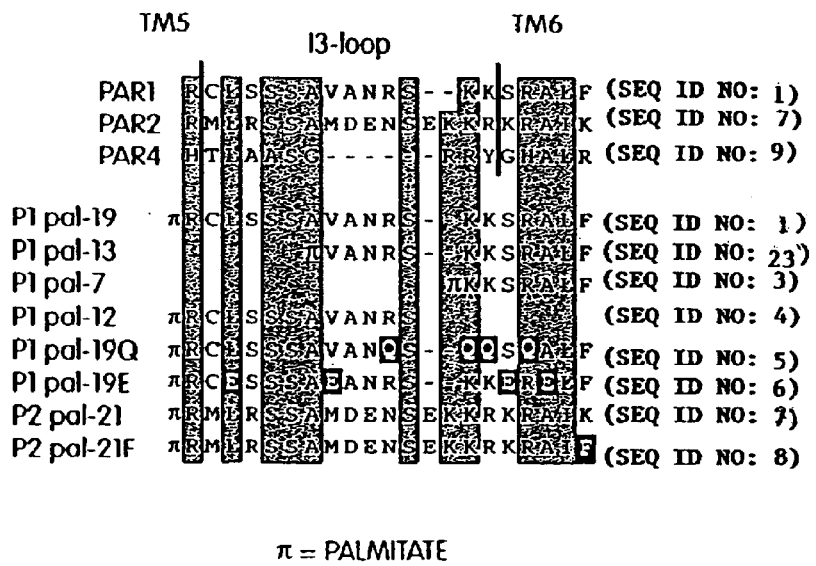
FIGS. 2A through 2G depict schematic representations of the alignment of i3 loops and adjacent transmembrane regions, as well as cell-penetrating ability of the peptides of the present invention.
Figure 2B:
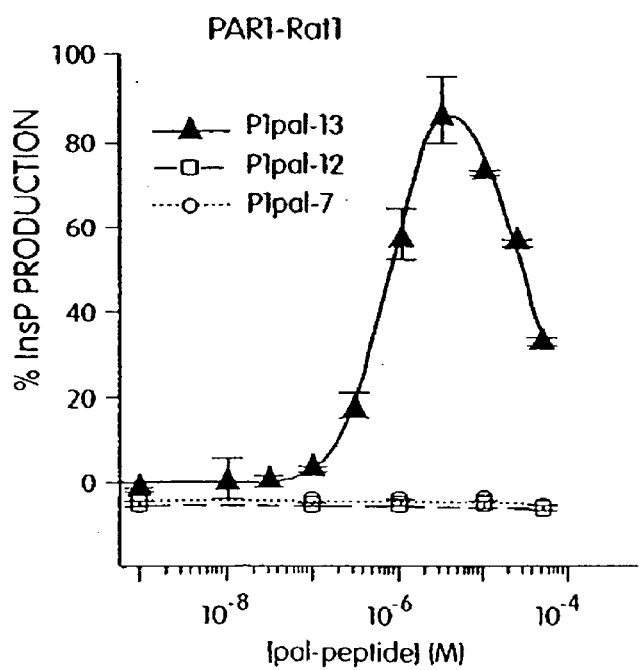
Figure 2C:
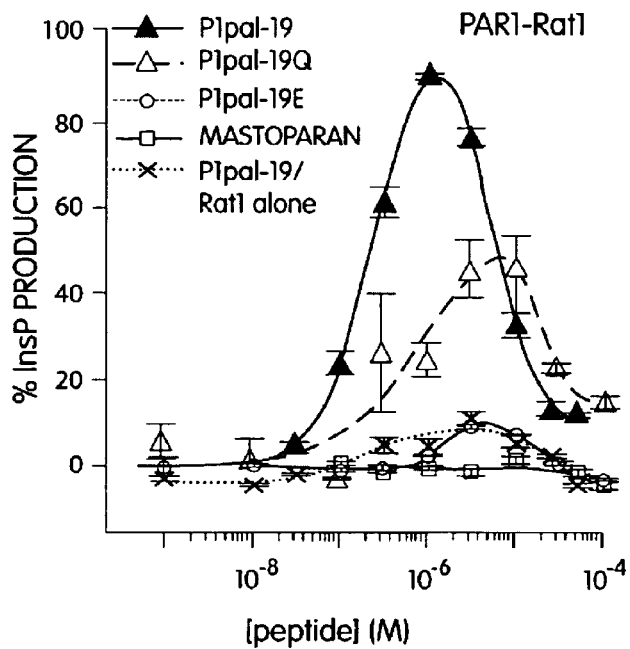
Figure 2D:
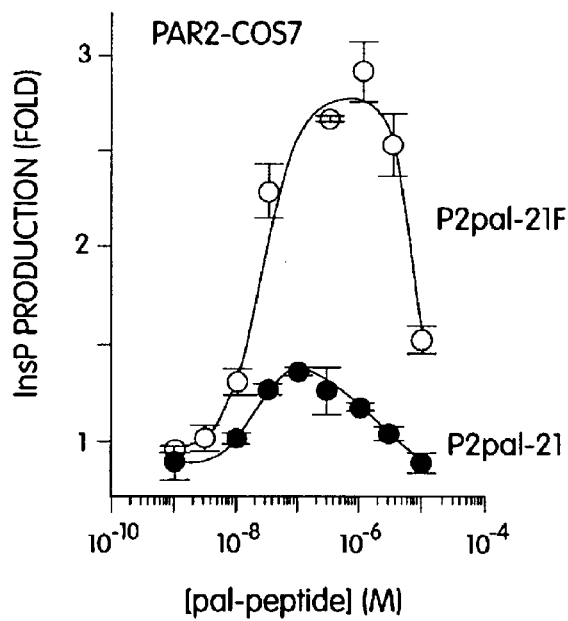
Figure 2E:
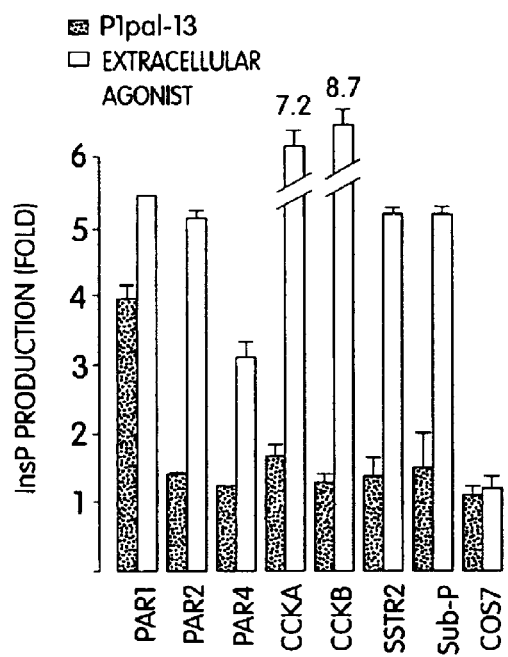
Figure 2F:
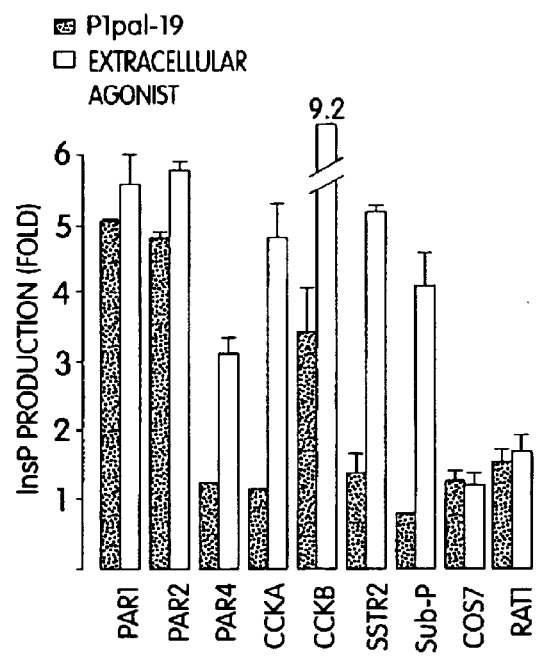
Figure 2G:
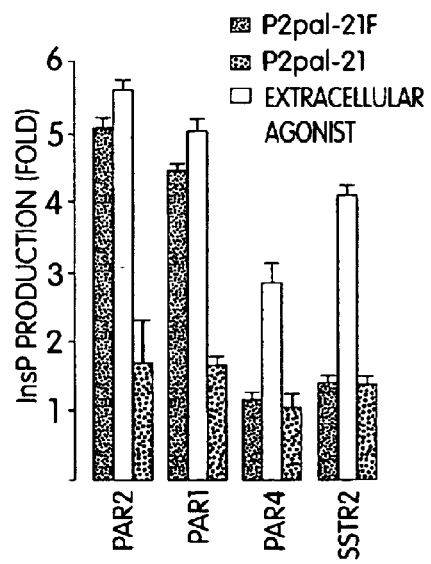

Quite interestingly, six of the newly tested wild-type pepducins were, at best, only partial agonists for their own GPCR with maximal efficacies of ~12–35% (Table 1, FIG. 7) including the P2pal-21 pepducin (FIG. 2D). However, we had previously demonstrated that the PAR1 pepducin, P1pal-19, could robustly activate PAR2 (FIG. 2F) indicating that selective introduction of mutations into P2pal-21 might create a full agonist for PAR2. An alignment of the i3 loops of PAR1 and PAR2 (FIG. 2A) revealed several sequence differences. We were quite excited to discover that a point mutation of the C-terminal lysine to phenylalanine imparted full agonist activity (FIG. 2D) to the PAR2 pepducin P2pal-21F. This pepducin also activated PAR1 but not PAR4 nor SSTR2 (FIG. 2G). Similar C-terminal point mutations of Lys/Arg to Phe conferred partial agonist activity to the pepducins of SSTR2, and CCKA and improved the potency of the CCKB pepducin by 15-fold (Table 1). To summarize, from this screen of seven diverse GPCRs, we have demonstrated full agonists for PAR1 and PAR2, partial agonists for MC4, SSTR2, CCKA, and CCKB, and full antagonists for PAR1, PAR2, PAR4 and SSTR2 (Table 1, FIG. 7). Thus, we anticipate that pepducin inhibitors and agonists will be applicable to a broad range of GPCRs which can couple to Gq, Gi, Gs, and G12/13.

The GPCR of the present invention may be any polypeptide derived from any cells of a human being and organisms (e.g., guinea pig, rat, mouse, chicken, rabbit, pig, sheep, cattle, monkey, virus, fungi, insects, plants, bacteria, etc.), for example, splenic cell, nerve cell, glia cell, beta cell of pancreas, marrow cell, mesangial cell, Langerhans' cell, epidermic cell, epithelial cell, endothelial cell, fibroblast, fibrocyte, muscular cell, fat cell, immunocyte (e.g., macrophage, T cell, B cell, natural killer cell, mast cell, neutrophil, basophil, eosinophilic leukocyte, monocyte, etc.), megakaryocyte, synovial cell, chondrocyte, osteocyte, osteoblast, osteoclast, mammary gland cell, hepatocyte, or interstitial cells or precursor cells, stem cells or cancer cells thereof and the like; and any tissues containing such cells, for example, brain, various parts of the brain (e.g., olfactory bulb, amygdala, cerebral basal ganglia, hippocampus, thalamus, hypothalamus, substhanlamic nucleus, cerebral cortex, medulla, cerebellum, occipital pole, frontal lobe, putamen, caudate nucleus, corpus callosum, substantia nigra), spinal cord, pituitary, stomach, pancreas, kidney, liver, genital organs, thyroid gland, gallbladder, bone marrow, adrenal gland, skin, muscle, lung, digestive tract, blood vessel, heart, thymus, spleen, submandibular gland, peripheral blood, peripheral blood leukocyte, intestinal tract, prostate, testicle, testis, ovarium, placenta, uterus, bone, joint, small intestine, large intestine, skeletal muscle and the like, in particular, brain and various parts of the brain. And, the peptide may be a synthetic one, or have substantially the same activity or structure of a GPCR. Examples of substantially the same activity include ligand binding activity, signal information transmission activity and the like. The wording "substantially the same" means that the natures of their activities are equal to one another. Therefore, quantitative factors such as degrees of ligand binding activity and signal information transmission activity may differ from one another.

Polypeptides of the Invention

A GPCR peptide of the invention includes any known or unknown GPCR-like peptide comprised of GPCR extracellular loops/domains with adjacent transmembrane amino acids and not including native extracellular ligand, and intracellular loops/domains with adjacent transmembrane amino acids. The transmembrane amino acids of the GPCR peptide may be substituted in some cases with other hydrophobic amino acid residues. The invention also includes a mutant or variant GPCR peptide that maintains its GPCR-like activities and physiological functions, or a functional fragment thereof. In some embodiments, up to 25% or more of the residues may be so changed in the mutant or variant peptide. In some embodiments, the GPCR peptide according to the invention is a mature polypeptide.

In general, a GPCR-like variant that preserves GPCR-like function includes any variant in which residues at a particular position in the sequence have been substituted by other amino acids, and further include the possibility of inserting an additional residue or residues between two residues of the parent protein as well as the possibility of deleting one or more residues from the parent sequence. Any amino acid substitution, insertion, or deletion is encompassed by the invention. In favorable circumstances, the substitution is a conservative substitution as defined above.

One aspect of the invention pertains to isolated GPCR peptides, and biologically active portions thereof, or derivatives, fragments, analogs or homologs thereof. Also provided are polypeptide fragments suitable for use as immunogens to raise anti-GPCR antibodies. In one embodiment, native GPCR peptides can be isolated from cells or tissue sources by an appropriate purification scheme using standard protein purification techniques. In another embodiment, GPCR peptides are produced by recombinant DNA techniques. Alternative to recombinant expression, a GPCR peptide or polypeptide can be synthesized chemically using standard peptide synthesis techniques.

An "isolated" or "purified" peptide or biologically active portion thereof is substantially free of cellular material or other contaminating proteins from the cell or tissue source from which the GPCR peptide is derived, or substantially free from chemical precursors or other chemicals when chemically synthesized. The language "substantially free of cellular material" includes preparations of GPCR peptide in which the peptide is separated from cellular components of the cells from which it is isolated or recombinantly produced. In one embodiment, the language "substantially free of cellular material" includes preparations of GPCR peptide having less than about 30% (by dry weight) of non-GPCR protein (also referred to herein as a "contaminating protein"), more preferably less than about 20% of non-GPCR protein, still more preferably less than about 10% of non-GPCR protein, and most preferably less than about 5% non-GPCR protein. When the GPCR peptide or biologically active portion thereof is recombinantly produced, it is also preferably substantially free of culture medium, i.e., culture medium represents less than about 20%, more preferably less than about 10%, and most preferably less than about 5% of the volume of the peptide preparation.

The language "substantially free of chemical precursors or other chemicals" includes preparations of GPCR peptide in which the peptide is separated from chemical precursors or other chemicals that are involved in the synthesis of the peptide. In one embodiment, the language "substantially free of chemical precursors or other chemicals" includes preparations of GPCR peptide having less than about 30% (by dry weight) of chemical precursors or non-GPCR chemicals, more preferably less than about 20% chemical precursors or non-GPCR chemicals, still more preferably less than about 10% chemical precursors or non-GPCR chemicals, and most preferably less than about 5% chemical precursors or non-GPCR chemicals.

Chimeric and Fusion Peptides of the Invention

The invention provides GPCR-based chimeric or fusion peptides (i.e. pepducins). As used herein, a GPCR "chimeric peptide" or "fusion peptide or pepducin" comprises a peptide fragment from a GPCR operatively linked to a non-GPCR-hydrophobic moiety. A "peptide fragment from a GPCR" refers to a polypeptide having an amino acid sequence corresponding to any known or unknown GPCR without containing native extracellular ligand, whereas a "non-GPCR moiety" refers to any hydrophobic tether, lipid, polypeptide or small molecule that is not substantially homologous to any GPCR protein. Hydrophobic tethers could include, but are not restricted to any lipid or acyl moiety such as phospholipids, steroids, sphingosines, ceramides, octyl-glycine, 2-cyclohexylalanine, benzolylphenylalanine, propionoyl ($C_3$); butanoyl ($C_4$); pentanoyl ($C_5$); caproyl ($C_6$); heptanoyl ($C_7$); capryloyl ($C_8$); nonanoyl ($C_9$); capryl ($C_{10}$); undecanoyl ($C_{11}$); lauroyl ($C_{12}$); tridecanoyl ($C_{13}$); myristoyl ($C_{14}$); pentadecanoyl ($C_{15}$); palmitoyl ($C_{16}$); phtanoyl (($CH_3$)$_4$); heptadecanoyl ($C_{17}$); stearoyl ($C_{18}$); nonadecanoyl ($C_{19}$); arachidoyl ($C_{20}$); heniecosanoyl ($C_{21}$); behenoyl ($C_{22}$); trucisanoyl ($C_{23}$); and lignoceroyl ($C_{24}$); wherein said hydrophobic moiety is attached to said chimeric polypeptide with amide bonds, sulfhydryls, amines, alcohols, phenolic groups, or carbon-carbon bonds. Equally, the hydrophobic moiety is either transmembrane domain 5 of the GPCR or a fragment thereof or a palmitate moiety.

Within a GPCR fusion peptide the peptide fragment from a GPCR can correspond to all or a portion of a GPCR protein without containing native extracellular ligand. In one embodiment, a GPCR fusion peptide comprises at least one biologically active portion of a GPCR protein. In another embodiment, a GPCR fusion peptide comprises at least two biologically active portions of a GPCR protein. The non-GPCR polypeptide can be fused to the N-terminus and/or C-terminus of the GPCR polypeptide. Such fusion peptides can be further utilized in screening assays for compounds that modulate GPCR activity (such assays are described in detail below).

In another embodiment, the fusion peptide is a GST-GPCR fusion peptide in which the GPCR sequences are fused to the C-terminus of the GST (i.e., glutathione S-transferase) or $His_{6-12}$ sequences. Such fusion peptides can facilitate the stable production and purification of recombinant GPCR. Alternatively, the fusion peptide is expressed as tandomly repeated (n=1–30) polypeptides, separated by a chemically-cleavable amino acid linker, such as methionine, and attached to carrier protein, KSI, and $His_6$ tag. These can be prepared according to methods known to those skilled in the art, for example, as described in U.S. Pat. No. 5,648,244: Production, Purification, Cleavage, and Use of Fusion Peptides; Kuliopulos, A. & Walsh, C. T. (1997), which is incorporated herein in its entirety.

A GPCR chimeric or fusion peptide of the invention can be produced by standard recombinant DNA techniques. For example, DNA fragments coding for the different polypeptide sequences are ligated together in-frame in accordance with conventional techniques, e.g., by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers that give rise to complementary overhangs between two consecutive gene fragments that can subsequently be annealed and reamplified to generate a chimeric gene sequence (see, for example, Ausubel et al. (eds.) CURRENT PROTOCOLS IN MOLECULAR BIOLOGY, John Wiley & Sons, 1992). Moreover, many expression vectors are commercially available that already encode a fusion moiety (e.g., a GST polypeptide, or KSI-X-$His_6$). A GPCR-encoding nucleic acid can be cloned into such an expression vector such that the fusion moiety is linked in-frame to the GPCR peptide.

GPCR Agonists and Antagonists

The present invention also pertains to variants of the GPCR peptides that function as either GPCR agonists (mimetics) or as GPCR antagonists. Variants of the GPCR peptide can be generated by mutagenesis, e.g., discrete point mutations or truncations or insertions of the GPCR peptide. An agonist of the GPCR can elicit substantially the same, or a subset of, the biological activities of the GPCR stimulated with authentic extracellular ligands. An antagonist of the GPCR can inhibit one or more of the activities of the naturally occurring form of the GPCR by, for example, competitively or non-competitively binding to a downstream or upstream member of a cellular signaling cascade which includes the GPCR itself, its ligand, and associated G protein. Thus, specific biological effects can be elicited by treatment with a variant of limited function. In one embodiment, treatment of a subject with a variant having a subset of the biological activities of the naturally occurring portion of the GPCR peptide has fewer side effects in a subject relative to treatment with the naturally occurring portion of the GPCR peptide.

Variants of the GPCR protein that function as either GPCR agonists (mimetics) or as GPCR antagonists can be identified by screening combinatorial libraries of mutants, truncation mutants, insertion mutants, of the GPCR peptide for GPCR agonist or antagonist activity. In one embodiment, a variegated library of GPCR peptide variants is generated by combinatorial mutagenesis at the nucleic acid level and is encoded by a variegated gene library. A variegated library of GPCR peptide variants can be produced by, for example, enzymatically ligating a mixture of synthetic oligonucleotides into gene sequences such that a degenerate set of potential GPCR peptide sequences is expressible as individual polypeptides, or alternatively, as a set of larger fusion proteins (e.g., for phage display) containing the set of GPCR peptide sequences therein. There are a variety of methods which can be used to produce libraries of potential GPCR peptide variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential GPCR peptide sequences. Methods for synthesizing degenerate oligonucleotides are known in the art (see, e.g., Narang (1983) *Tetrahedron* 39:3; Itakura et al. (1984) *Annu Rev Biochem* 53:323; Itakura et al. (1984) *Science* 198:1056; Ike et al. (1983) *Nucl Acid Res* 11:477.

Expression Vector, Host Cells and Pepducin/GCPR Peptide Isolation

An expression vector for any of the pepducins and/or GPCR peptides can be produced by, for example, (a) cutting out a target DNA fragment from the G protein coupled receptor protein-encoding DNA of the present invention and (b) ligating the target DNA fragment with the downstream site of a promoter in a suitable expression vector. The vector may include plasmids derived from *Escherichia coli* (e.g., pBR322, pBR325, pUC12, pUC13, etc.), plasmids derived from *Bacillus subtilis* (e.g., pUB110, pTP5, pC194, etc.), plasmids derived from yeasts (e.g., pSH19, pSH15, etc.), bacteriophages such as lambda-phage, and animal virus such as retrovirus, vaccinia virus and baculovirus.

According to the present invention, any promoter can be used as long as it is compatible with a host which is used for expressing a gene. When the host for the transformation is *E. coli*, the promoters are preferably trp promoters, lac promoters, recA promoters, etc. When the host for the transformation is the *Bacillus,* the promoters are preferably SPO1 promoters, SPO2 promoters, penP promoters, etc. When the host is an yeast, the promoters are preferably PHO5 promoters, PGK promoters, GAP promoters, ADH promoters, etc. When the host is an animal cell, the promoters include SV40-derived promoters, retrovirus promoters, metallothionein promoters, heat shock promoters, cytomegalovirus promoters, SRa promoters, etc. An enhancer can be effectively utilized for the expression.

As required, furthermore, a host-compatible signal sequence is added to the N-terminal side of the G protein coupled receptor protein. When the host is *E. coli*, the utilizable signal sequences may include alkaline phosphatase signal sequences, OmpA signal sequences, etc. When the host is the *Bacillus,* they may include alpha-amylase signal sequences, subtilisin signal sequences, etc. When the host is an yeast, they may include mating factor a signal sequences, invertase signal sequences, etc. When the host is an animal cell, they may include insulin signal sequences, alpha-interferon signal sequences, antibody molecule signal sequences, etc.

A transformant or transfectant is produced by using the vector thus constructed, which carries the G protein coupled receptor protein-encoding DNA of the present invention. The host may be, for example, *Escherichia* microorganisms, *Bacillus* microorganisms, yeasts, insect cells, animal cells, etc. Examples of the *Escherichia* and *Bacillus* microorganisms include *Escherichia coli* K12-DH1 [Proc. Natl. Acad. .3ci. USA, Vol. 60, 160 (1968)], JM103 [Nucleic Acids Research, Vol. 9, 309 (1981)], JA221 [Journal of Molecular Biology, Vol. 120, 517 (1978)], HB101 [Journal of Molecular Biology, Vol. 41, 459 (1969)], C600 [Genetics, Vol. 39, 440 (1954)], etc. Examples of the *Bacillus* microorganism are, for example, *Bacillus subtilis* MI114 [Gene, Vol. 24, 255 (1983)], 207-21 [Journal of Biochemistry, Vol. 95, 87 (1984)], etc. The yeast may be, for example, *Saccharomyces cerevisiae* AH22, AH22R-, NA87-11A, DKD-5D, 20B-12, etc. The insect may include a silkworm (*Bombyx mori* larva), [Maeda et al, Nature, Vol. 315, 592 (1985)] etc. The host animal cell may be, for example, monkey-derived cell line, COS-7, Vero, Chinese hamster ovary cell line (CHO cell), DHFR gene-deficient Chinese hamster cell line (dhfr CHO cell), mouse L cell, murine myeloma cell, human FL cell, etc.

Depending on the host cell used, transformation is done using standard techniques appropriate to such cells. Transformation of *Escherichia* microorganisms can be carried out in accordance with methods as disclosed in, for example, Proc. Natl. Acad. Sci. USA, Vol. 69, 2110 (1972), Gene, Vol. 17, 107 (1982), etc. Transformation of *Bacillus* microorganisms can be carried out in accordance with methods as disclosed in, for example, Molecular & General Genetics, Vol. 168, 111 (1979), etc. Transformation of the yeast can be carried out in accordance with methods as disclosed in, for example, Proc. Natl. Acad. Sci. USA, Vol. 75, 1929 (1978), etc. The insect cells can be transformed in accordance with methods as disclosed in, for example, Bio/Technology, 6, 47–55, 1988. The animal cells can be transformed by methods as disclosed in, for example, Virology, Vol. 52, 456, 1973, etc. The transformants or transfectants which are transformed with expression vectors containing a G protein coupled receptor protein-encoding DNA are produced according to the aforementioned techniques.

Cultivation of the transformant (transfectant) in which the host is *Escherichia* or *Bacillus* microorganism can be carried out suitably in a liquid culture medium. The culture medium may contains carbon sources, nitrogen sources, minerals, etc. necessary for growing the transformant. The carbon source may include glucose, dextrin, soluble starch, sucrose, etc. The nitrogen source may include organic or inorganic substances such as ammonium salts, nitrates, corn steep liquor, peptone, casein, meat extracts, bean-cakes, potato extracts, etc. Examples of the minerals may include calcium chloride, sodium dihydrogen phosphate, magnesium chloride, etc. It is further allowable to add yeasts, vitamines, growth-promoting factors, etc. It is desired that the culture medium is pH from about 5 to about 8.

The *Escherichia* microorganism culture medium is preferably an M9 medium containing, for example, glucose and casamino acid (Miller, Journal of Experiments in Molecular Genetics), 431–433, Cold Spring Harbor Laboratory, New York, 1972. Depending on necessity, the medium may be supplemented with drugs such as 3.beta.-indolyl acrylic acid in order to improve efficiency of the promoter. In the case of the *Escherichia* host, the cultivation is carried out usually at about 15 to 43.degree. C. for about 3 to 24 hours. As required, aeration and stirring may be applied. In the case of the *Bacillus* host, the cultivation is carried out usually at about 30 to 40.degree. C. for about 6 to 24 hours. As required, aeration and stirring may be also applied. In the case of the transformant in which the host is an yeast, the culture medium used may include, for example, a Burkholder minimum medium [Bostian, K. L. et al., Proc. Natl. Acad. Sci. USA, Vol. 77, 4505 (1980)], an SD medium containing 0.5% casamino acid [Bitter, G. A. et al., Proc. Natl. Acad. Sci. USA, Vol. 81, 5330 (1984)], etc. It is preferable that pH of the culture medium is adjusted to be from about 5 to about 8. The cultivation is carried out usually at about 20 to 35.degree. C. for about 24 to 72 hours. As required, aeration and stirring may be applied. In the case of the transformant in which the host is an insect, the culture medium used may include those obtained by suitably adding additives such as passivated (or immobilized) 10% bovine serum and the like to the Grace's insect medium (Grace, T. C. C., Nature, 195, 788 (1962)). It is preferable that pH of the culture medium is adjusted to be about 6.2 to 6.4. The cultivation is usually carried out at about 27.degree. C. for about 3 to 5 days. As desired, aeration and stirring may be applied. In the case of the transformant in which the host is an animal cell, the culture medium used may include MEM medium [Science, Vol. 122, 501 (1952)], DMEM medium [Virology, Vol. 8, 396 (1959)], RPMI 1640 medium [Journal of the American Medical Association, Vol. 199, 519 (1967)], 199 medium [Proceedings of the Society of the Biological Medicine, Vol. 73, 1 (.L950)], etc. which are containing, for example, about 5 to 23% of fetal calf serum. It is preferable that the pH is from about 6 to about 8. The cultivation is usually carried out at about 30 to 40.degree. C. for about 15 to 60 hours. As required, aeration and stirring may be applied.

Separation and purification of the pepducin or GPCR peptide from the above-mentioned cultures can be carried out according to methods described herein below. To extract the pepducins or GPCR peptides from the cultured microorganisms or cells, the microorganisms or cells are collected by known methods after the cultivation, suspended in a suitable buffer solution, disrupted by ultrasonic waves, lysozyme and/or freezing and thawing, etc. and, then, a crude extract of the G protein coupled receptor protein is obtained by centrifugation or filtration. Other conventional extracting or isolating methods can be applied. The buffer solution may contain a protein-denaturing agent such as urea or guanidine hydrochloride or a surfactant such as Triton X-100 (registered trademark, hereinafter often referred to as "TM").

In case where the pepducin or GPCR peptide is secreted into culture media, supernatant liquids are separated from the microorganisms or cells after the cultivation is finished and the resulting supernatant liquid is collected by widely known methods. The culture supernatant liquid and extract containing the pepducin or peptide can be purified by suitable combinations of widely known methods for separation, isolation and purification. The widely known methods of separation, isolation and purification may include methods which utilizes solubility, such as salting out or sedimentation with solvents methods which utilizes chiefly a difference in the molecular size or weight, such as dialysis, ultrafiltration, gel filtration and SDS-polyacrylamide gel electrophoresis, methods utilizing a difference in the electric charge, such as ion-exchange chromatography, methods utilizing specific affinity such as affinity chromatography, methods utilizing a difference in the hydrophobic property, such as inverse-phase high-performance liquid chromatography, and methods utilizing a difference in the isoelectric point such as isoelectric electrophoresis, etc.

In case where the pepducin or GPCR peptide thus obtained is in a free form, the free protein can be converted into a salt thereof by known methods or method analogous thereto. In case where the pepducin or GPCR peptide thus obtained is in a salt form vice versa, the protein salt can be converted into a free form or into any other salt thereof by known methods or method analogous thereto.

The pepducin or GPCR peptide produced by the transformant can be arbitrarily modified or a polypeptide can be partly removed therefrom, by the action of a suitable protein-modifying enzyme before or after the purification. The protein-modifying enzyme may include trypsin, chymotrypsin, arginyl endopeptidase, protein kinase, glycosidase, etc. The activity of the pepducin or GPCR peptide thus formed can be measured by experimenting the coupling (or binding) with a ligand or by enzyme immunoassays (enzyme linked immunoassays) using specific antibodies.

Polypeptide Libraries

In addition, libraries of fragments of the GPCR protein coding sequence can be used to generate a variegated population of GPCR fragments for screening and subsequent selection of variants of a GPCR protein. In one embodiment, a library of coding sequence fragments can be generated by treating a double stranded PCR fragment of a GPCR coding sequence with a nuclease under conditions wherein nicking occurs only about once per molecule, denaturing the double stranded DNA, renaturing the DNA to form double stranded DNA that can include sense/antisense pairs from different nicked products, removing single stranded portions from reformed duplexes by treatment with S1 nuclease, and ligating the resulting fragment library into an expression vector. By this method, an expression library can be derived which encodes N-terminal and internal fragments of various sizes of the GPCR peptide.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of GPCR peptides. The most widely used techniques, which are amenable to high throughput analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recrusive ensemble mutagenesis (REM), a new technique that enhances the frequency of functional mutants in the libraries, can be used in combination with the screening assays to identify GPCR peptide variants (Arkin and Yourvan (1992) PNAS 89:7811–7815; Delgrave et al. (1993) Protein Engineering 6:327–331).

Pharmaceutical Compositions

The pepducins and GPCR peptides (also referred to herein as "active compounds") of the invention, and derivatives, fragments, analogs and homologs thereof, can be incorporated into pharmaceutical compositions suitable for administration. Such compositions typically comprise the nucleic acid molecule, protein, or antibody and a pharmaceutically acceptable carrier. As used herein, "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, Ringer's solutions, dextrose solution, and 5% human serum albumin. Liposomes, emulsions, and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

Particularly useful liposomes can be generated by the reverse-phase evaporation method with a lipid composition comprising phosphatidylcholine, cholesterol, and PEG-derivatized phosphatidylethanolamine (PEG-PE). Liposomes are extruded through filters of defined pore size to yield liposomes with the desired diameter. A chemotherapeutic agent (such as Doxorubicin) is optionally contained within the liposome. See Gabizon et al., J. National Cancer Inst., 81(19): 1484 (1989).

A pharmaceutical composition of the invention is formulated to be compatible with its intended route of administration. Examples of routes of administration include parenteral, e.g., intravenous, intradermal, subcutaneous, oral (e.g., inhalation), transdermal (i.e., topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a GPCR peptide or anti-GPCR-peptide antibody) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The nucleic acid molecules of the invention can be inserted into vectors and used as gene therapy vectors. Gene therapy vectors can be delivered to a subject by, for example, intravenous injection, local administration (see, e.g., U.S. Pat. No. 5,328,470) or by stereotactic injection (see, e.g., Chen, et al., 1994. *Proc. Natl. Acad. Sci. USA* 91: 3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells that produce the gene delivery system.

The pepducins and GPCR peptides identified by the screening assays disclosed herein, can be administered for the treatment of various disorders in the form of pharmaceutical compositions. Principles and considerations involved in preparing such compositions, as well as guidance in the choice of components are provided, for example, in Remington: The Science And Practice Of Pharmacy 19th ed. (Alfonso R. Gennaro, et al., editors) Mack Pub. Co., Easton, Pa.: 1995; Drug Absorption Enhancement: Concepts, Possibilities, Limitations, And Trends, Harwood Academic Publishers, Langhorne, Pa., 1994; and Peptide And Protein Drug Delivery (Advances In Parenteral Sciences, Vol. 4), 1991, M. Dekker, New York. The formulation herein can also contain more than one active compound as necessary for the particular indication being treated, preferably those with complementary activities that do not adversely affect each other. Alternatively, or in addition, the composition can comprise an agent that enhances its function, such as, for example, a cytotoxic agent, cytokine, chemotherapeutic agent, or growth-inhibitory agent. Such molecules are suitably present in combination in amounts that are effective for the purpose intended. The active ingredients can also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles, and nanocapsules) or in macroemulsions.

The formulations to be used for iv vivo administration must be sterile. This is readily accomplished by filtration through sterile filtration membranes.

Sustained-release preparations can be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly (vinylalcohol)), polylactides (U.S. Pat. No. 3,773,919), copolymers of L-glutamic acid and ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(–)-3-hydroxybutyric acid. While polymers such as ethylene-vinyl acetate and lactic acid-glycolic acid enable release of molecules for over 100 days, certain hydrogels release proteins for shorter time periods.

The pharmaceutical compositions can be included in a container, pack, or dispenser together with instructions for administration.

Screening and Detection Methods

The isolated nucleic acid molecules of the invention can be used to express the GPCR peptide (e.g., via a recombinant expression vector in a host cell in gene therapy applications), to detect GPCR mRNA (e.g., in a biological sample) or a genetic lesion in a GPCR gene, and to modulate GPCR activity, as described further, below. In addition, the GPCR peptides can be used to screen drugs or compounds that modulate GPCR activity or expression as well as to treat disorders characterized by insufficient or excessive production of GPCR protein or production of GPCR protein forms that have decreased or aberrant activity compared to GPCR wild-type protein. In addition, the anti-GPCR-peptide antibodies of the invention can be used to detect and isolate GPCR peptides and modulate GPCR activity. For example, GPCR activity includes growth and differentiation, metabolic regulation, chemotaxis, blood coagulation, antibody production, tumor growth and invasion.

The invention further pertains to novel agents identified by the screening assays described herein and uses thereof for treatments as described, vide supra.

Screening Assays

The invention provides a method (also referred to herein as a "screening assay") for identifying modulators, i.e., candidate or test compounds or agents (e.g., peptides, peptidomimetics, small molecules or other drugs) that bind to GPCRs or have a stimulatory or inhibitory effect on, e.g., GPCR protein expression or GPCR activity. The invention also includes compounds identified in the screening assays described herein.

In one embodiment, the invention provides assays for screening candidate or test compounds which bind to or modulate the activity of the membrane-bound form of a pepducin-GPCR complex or biologically-active portion thereof. The test compounds of the invention can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds. See, e.g., Lam, 1997. *Anticancer Drug Design* 12: 145.

A "small molecule" as used herein, is meant to refer to a composition that has a molecular weight of less than about 5 kD and most preferably less than about 4 kD. Small molecules can be, e.g., nucleic acids, peptides, polypeptides, peptidomimetics, carbohydrates, lipids or other organic or inorganic molecules. Libraries of chemical and/or biological mixtures, such as fungal, bacterial, or algal extracts, are known in the art and can be screened with any of the assays of the invention.

Examples of methods for the synthesis of molecular libraries can be found in the art, for example in: DeWitt, et al., 1993. *Proc. Natl. Acad Sci. U.S.A.* 90: 6909; Erb, et al., 1994. *Proc. Natl. Acad. Sci. U.S.A.* 91: 11422; Zuckermann, et al., 1994. *J. Med. Chem.* 37: 2678; Cho, et al., 1993. *Science* 261: 1303; Carrell, et al., 1994. *Angew. Chem. Int. Ed. Engl.* 33: 2059; Carell, et al., 1994. *Angew. Chem. Int. Ed. Engl.* 33: 2061; and Gallop, et al., 1994. *J. Med. Chem.* 37: 1233.

Libraries of compounds may be presented in solution (e.g., Houghten, 1992. *Biotechniques* 13: 412–421), or on beads (Lam, 1991. *Nature* 354: 82–84), on chips (Fodor, 1993. *Nature* 364: 555–556), bacteria (Ladner, U.S. Pat. No. 5,223,409), spores (Ladner, U.S. Pat. No. 5,233,409), plasmids (Cull, et al., 1992. *Proc. Natl. Acad. Sci. USA* 89: 1865–1869) or on phage (Scott and Smith, 1990. *Science* 249: 386–390; Devlin, 1990. *Science* 249: 404–406; Cwirla, et al., 1990. *Proc. Natl. Acad. Sci. USA.* 87: 6378–6382; Felici, 1991. *J. Mol. Biol.* 222: 301–310; Ladner, U.S. Pat. No. 5,233,409.).

In one embodiment, an assay is a cell-based assay in which a cell which expresses a membrane-bound form of a GPCR, or a biologically-active portion thereof on the cell surface, plus a pepducin, is contacted with a test compound and the ability of the test compound to bind to the GPCR and displace the pepducin determined. The test compound could bind at the extracellular surface, transmembrane domains, or intracellular surfaces of the GPCR target and inhibit or enhance the pepducin activation of the GPCR. The cell, for example, can be of mammalian origin or a yeast cell. Determining the ability of the test compound to displace the pepducin from the GPCR protein can be accomplished, for example, by coupling the pepducin to a radioisotope or enzymatic label such that binding of the test compound displaces the pepducin from the GPCR or biologically-active portion thereof. Alternatively, the test compounds can be labeled with $^{125}I$, $^{35}S$, $^{14}C$, or $^{3}H$, either directly or indirectly, and the pepducin could displace the radio-labeled test compound from the GPCR and the free radio-labeled test compound detected by direct counting of radioemission or by scintillation counting. Alternatively, test compounds can be enzymatically-labeled with, for example, horseradish peroxidase, alkaline phosphatase, or luciferase, and the enzymatic label detected by increases or decreases in conversion of an appropriate substrate to product upon addition of pepducin.

In another embodiment, an assay is a cell-based assay comprising contacting a cell expressing a membrane-bound form of GPCR protein, or a biologically-active portion thereof, on the cell surface with a test compound and determining the ability of the test compound to modulate (e.g., stimulate or inhibit) the binding, activity of the pepducin for the GPCR As used herein, a "target molecule" is a molecule with which a GPCR protein binds or interacts in nature, for example, a molecule on the surface of a cell which expresses a GPCR interacting protein, a molecule on the surface of a second cell, a molecule in the extracellular milieu, a molecule associated with the internal surface of a cell membrane or a cytoplasmic molecule. A GPCR target molecule can be a non-GPCR molecule or a GPCR peptide of the invention. In one embodiment, a GPCR target molecule is a component of a signal transduction pathway that facilitates transduction of an extracellular signal (e.g. a signal generated by binding of a compound to a membrane-bound GPCR) through the cell membrane and into the cell. The target, for example, can be a second intercellular protein that has catalytic activity or a protein that facilitates the association of downstream signaling molecules with GPCR.

Determining the ability of the test molecule to interact with a GPCR target molecule can be accomplished by one of the methods described above for determining direct binding. In one embodiment, determining the ability of the test molecule to inhibit the GPCR peptide interaction with a GPCR target molecule can be accomplished by determining the activity of the target GCPR-pepducin complex. For example, the activity of the target molecule can be determined by inhibiting GPCR-peptide induction of a cellular second messenger of the GPCR target (i.e. intracellular $Ca^{2+}$, diacylglycerol, $IP_3$, etc.), detecting catalytic/enzymatic activity dependent on GPCR activation or inhibition, detecting the induction or inhibition of a reporter gene (comprising a GPCR-responsive regulatory element operatively linked to a nucleic acid encoding a detectable marker, e.g., luciferase), or detecting a cellular response, for example, cell survival, cellular differentiation, or cell proliferation.

In yet another embodiment, an assay of the invention is a cell-free assay comprising contacting a GPCR peptide or biologically-active portion thereof with a test compound and determining the ability of the test compound to bind to the GPCR or biologically-active portion thereof. Binding of the test compound to the GPCR can be determined either directly or indirectly as described above. In one such embodiment, the assay comprises contacting the pepducin plus the GPCR or biologically-active portion thereof with a known compound which binds GPCR to form an assay mixture, contacting the assay mixture with a test compound, and determining the ability of the test compound to interact with a GPCR protein, wherein determining the ability of the test compound to interact with a GPCR protein comprises determining the ability of the test compound to preferentially bind to GPCR or biologically-active portion thereof as compared to the known compound.

In still another embodiment, an assay is a cell-free assay comprising contacting GPCR peptide or biologically-active portion thereof with a test compound and determining the ability of the test compound to modulate (e.g. stimulate or inhibit) the activity of the GPCR protein or biologically-active portion thereof. Determining the ability of the test compound to modulate the activity of GPCR can be accomplished, for example, by determining the ability of the GPCR peptide to bind to a GPCR target molecule by one of the methods described above for determining direct binding. In an alternative embodiment, determining the ability of the test compound to modulate the activity of GPCR peptide can be accomplished by determining the ability of the GPCR peptide to further modulate a GPCR target molecule. For example, the catalytic/enzymatic activity of the target molecule on an appropriate substrate can be determined as described above.

In yet another embodiment, the cell-free assay comprises contacting the GPCR peptide or biologically-active portion thereof with a known compound which binds the GPCR to form an assay mixture, contacting the assay mixture with a test compound, and determining the ability of the test compound to interact with a GPCR, wherein determining the ability of the test compound to interact with a GPCR comprises determining the ability of the GPCR peptide to preferentially bind to or modulate the activity of a GPCR target molecule.

The cell-free assays of the invention are amenable to use of both the soluble form or the membrane-bound form of GPCR protein. In the case of cell-free assays comprising the membrane-bound form of GPCR protein, it may be desirable to utilize a solubilizing agent such that the membrane-bound form of GPCR protein is maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)$_n$, N-dodecyl--N,N-dimethyl-3-ammonio-1-propane sulfonate, 3-(3-cholamidopropyl) dimethylamminiol-1-propane sulfonate (CHAPS), or 3-(3-cholamidopropyl) dimethylamminiol-2-hydroxy-1-propane sulfonate (CHAPSO).

In more than one embodiment of the above assay methods of the invention, it may be desirable to immobilize either GPCR peptide or its target molecule to facilitate separation of complexed from uncomplexed forms of one or both of the proteins, as well as to accommodate automation of the assay. Binding of a test compound to GPCR protein, or interaction of GPCR protein with a pepducin in the presence and absence of a candidate compound, can be accomplished in any vessel suitable for containing the reactants. Examples of such vessels include microtiter plates, test tubes, and microcentrifuge tubes. In one embodiment, a fusion protein can be provided that adds a domain that allows one or both of the proteins to be bound to a matrix. For example, GST-GPCR fusion peptides or GST-target fusion proteins can be adsorbed onto glutathione sepharose beads (Sigma Chemical, St. Louis, Mo.) or glutathione derivatized microtiter plates, that are then combined with the test compound or the test compound and either the non-adsorbed target protein or GPCR peptide, and the mixture is incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly, for example, as described, vide supra. Alternatively, the complexes can be dissociated from the matrix, and the level of GPCR peptide binding or activity determined using standard techniques.

Other techniques for immobilizing proteins on matrices can also be used in the screening assays of the invention. For example, either the GPCR peptide or its target molecule can be immobilized utilizing conjugation of biotin and streptavidin. Biotinylated GPCR peptide or target molecules can be prepared from biotin-NHS (N-hydroxy-succinimide) using techniques well-known within the art (e.g., biotinylation kit, Pierce Chemicals, Rockford, Ill.), and immobilized in the wells of streptavidin-coated 96 well plates (Pierce Chemical). Alternatively, antibodies reactive with GPCR peptide or target molecules, but which do not interfere with binding of the GPCR peptide to its cognate GPCR, can be derivatized to the wells of the plate, and unbound target or GPCR peptide trapped in the wells by antibody conjugation. Methods for detecting such complexes, in addition to those described above for the GST-immobilized complexes, include immunodetection of complexes using antibodies reactive with the GPCR peptide or target molecule, as well as enzyme-linked assays that rely on detecting an enzymatic activity associated with the GPCR peptide or target molecule.

In another embodiment, modulators of GPCR protein expression are identified in a method wherein a cell is contacted with a candidate compound and the expression of GPCR mRNA or protein in the cell is determined. The level of expression of GPCR mRNA or protein in the presence of the candidate compound is compared to the level of expression of GPCR mRNA or protein in the absence of the candidate compound. The candidate compound can then be identified as a modulator of GPCR mRNA or protein expression based upon this comparison. For example, when expression of GPCR mRNA or protein is greater (i.e., statistically significantly greater) in the presence of the candidate compound than in its absence, the candidate compound is identified as a stimulator of GPCR mRNA or protein expression. Alternatively, when expression of GPCR mRNA or protein is less (statistically significantly less) in the presence of the candidate compound than in its absence, the candidate compound is identified as an inhibitor of GPCR mRNA or protein expression. The level of GPCR mRNA or protein expression in the cells can be determined by methods described herein for detecting GPCR mRNA or protein.

Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described below. All publications, patent applications, patents, and other references mentioned herein are incorporated by reference in their entirety. In the case of conflict, the present Specification, including definitions, will control. In addition, the materials, methods, and examples are illustrative only and not intended to be limiting.

The invention will be further illustrated in the following non-limiting examples.

EXAMPLES

Example 1

Construction of Pepducins

Figure 1B:
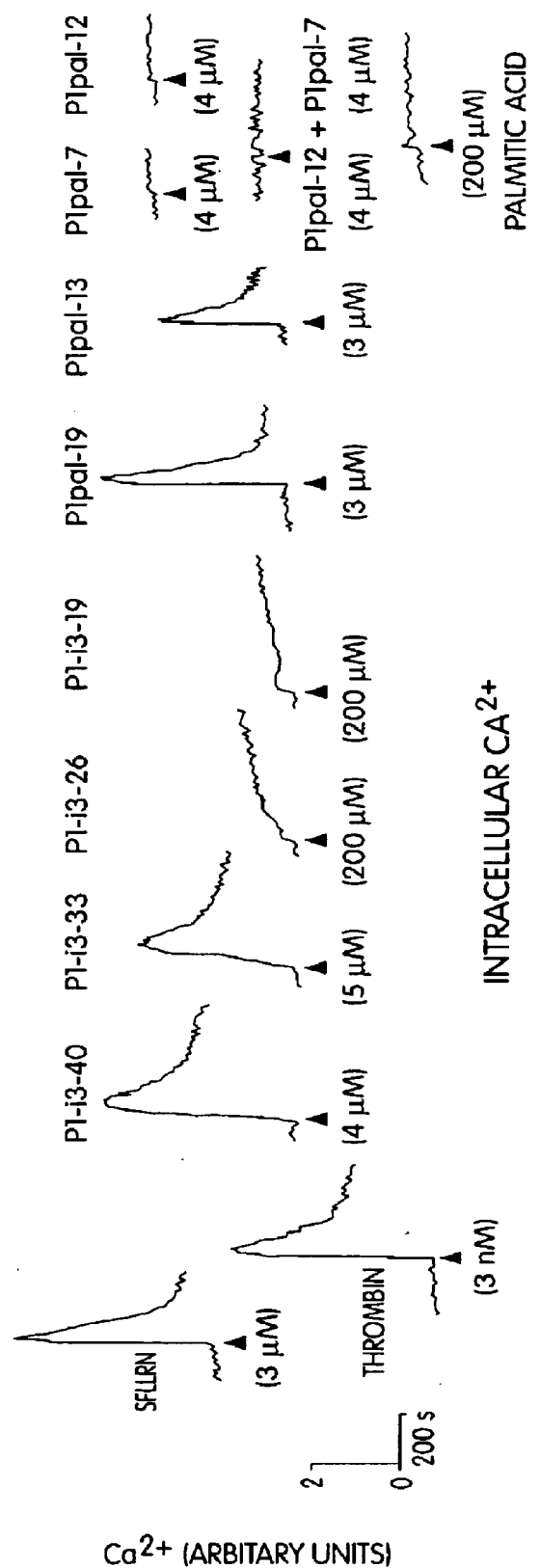
Figure 1C:
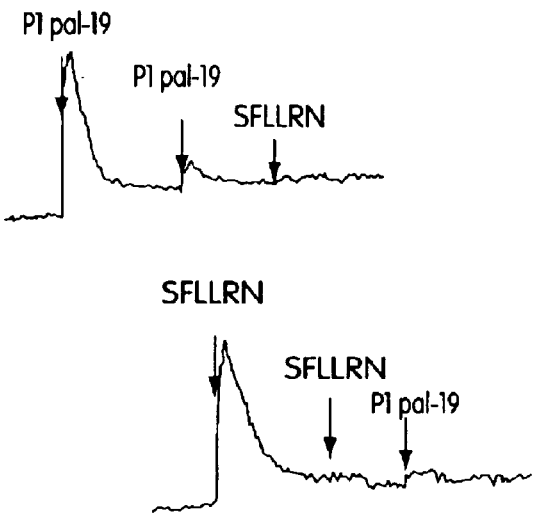

An i3 peptide, designated P1-i3-40, was constructed containing the adjacent transmembrane alpha-helical amino acids from the TM5 of PAR1. As a primary screen for biological activity, the ability of P1-i3-40 was tested for it's ability to stimulate platelet activation by monitoring intracellular Ca2+. The composition of the peptides used in this study are shown on the right and their corresponding effects on platelet Ca2+ are shown immediately below in FIG. 1. Platelets from healthy volunteer donors were isolated by gel filtration chromatography and Ca2+ measurements were performed as described (A. Kuliopulos et al., *Biochemistry* 38, 4572–4585 (1999)). Intracellular Ca2+ concentration was monitored as the ratio of fluorescence excitation intensity at 340/380 nm. When added to platelets, the P1-i3-40 peptide causes a rapid intracellular Ca2+ transient (Ca2+i) that mimics the Ca2+i response generated by thrombin (FIG. 1B). The Ca2+i transient has no measurable lag phase (<5 s) and the maximum Ca2+i is saturable. A series of progressively truncated versions of P1-i3-40 were then made in order to determine whether the N-terminal hydrophobic region was required for activity. The P1-i3-19 peptide, which completely lacks hydrophobic N-terminal residues, causes little stimulation of Ca2+ fluxes (FIG. 1B). The P1-i3-26 peptide with seven N-terminal hydrophobic residues, which would be expected to partition to only the outside leaflet of the lipid bilayer, gives a minor, unregulated Ca2+i response. In contrast, the P1-i3-33 peptide has similar potency to the P1-i3-40 peptide demonstrating that 14 hydrophobic amino acid residues confer full in vivo activity to the i3 intracellular loop. Studies with short membrane-translocating sequences have shown that 11–12 hydrophobic amino acid residues are sufficient to transfer proteins (15–120 kDa) into intact cells (M. Rojas, J. P. Donahue, Z. Tan, Y.-Z. Lin, *Nat. Biotech.* 16, 370–375 (1998).) and tissues of mice (S. R. Schwarze, A. Ho, A. Vocero-Akbani, S. F. Dowdy, *Science* 285, 156–159 (1999).

N-terminal hydrophobic residues from the TM5 helix were then replaced with a palmit te lipid ($C_{16}H_{31}O$) to drastically reduce the size of the i3 peptides. Palmitoylated peptides were synthesized y standard fmoc solid phase synthetic methods with C-terminal amides. Palmitic acid was dissolved in 50% N-methyl pyrolidone/50% methylene chloride and coupled overnight to the deprotected N-terminal amine of the peptide. After cleavage from the resin, palmitoylated peptides were purified to >95% purity by C18 or C4 reverse phase chromatography. As shown in FIG. 1B, the palmitoylated i3 loop peptide, P1pal-19 causes a rapid Ca2+i transient that is identical in profile to that caused by the extracellular PAR1 ligand, SFLLRN (SEQ ID NO:24). In addition, P1pal-19 fully activates platelet aggregation (FIG. 1D) with an ECS of 8±3 micromolar. Individual aggregation traces of platelets stimulated with 10 Micromolar of indicated petides or palmitic acid and platelet aggregation was monitored as % light transmittance of stinned platelets at 37° C. as described (L. Covic, A. L. Gresser, A. Kuliopulos, *Biochemistry* 39, 5458–5467 (2000).). P1pal-19 completely inhibits the subsequent Ca2+i response to 30 micromolar SFLLRN (SEQ ID NQ:24) (FIG. 1C) due to desensitization of PAR1. Similarly, prestimulation with SFLLRN (SEQ ID NO:24) completely desensitize the platelets to P1pal -19. Palmitic acid by itself has no effect on Ca 2+i and platelet aggregation (FIGS. 1B. D).

Figure 1D:
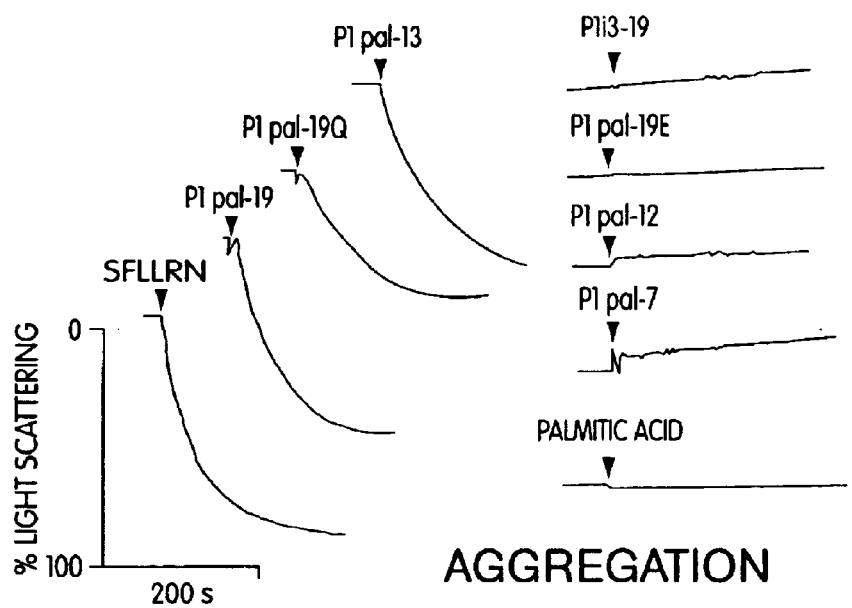
Figure 1E:
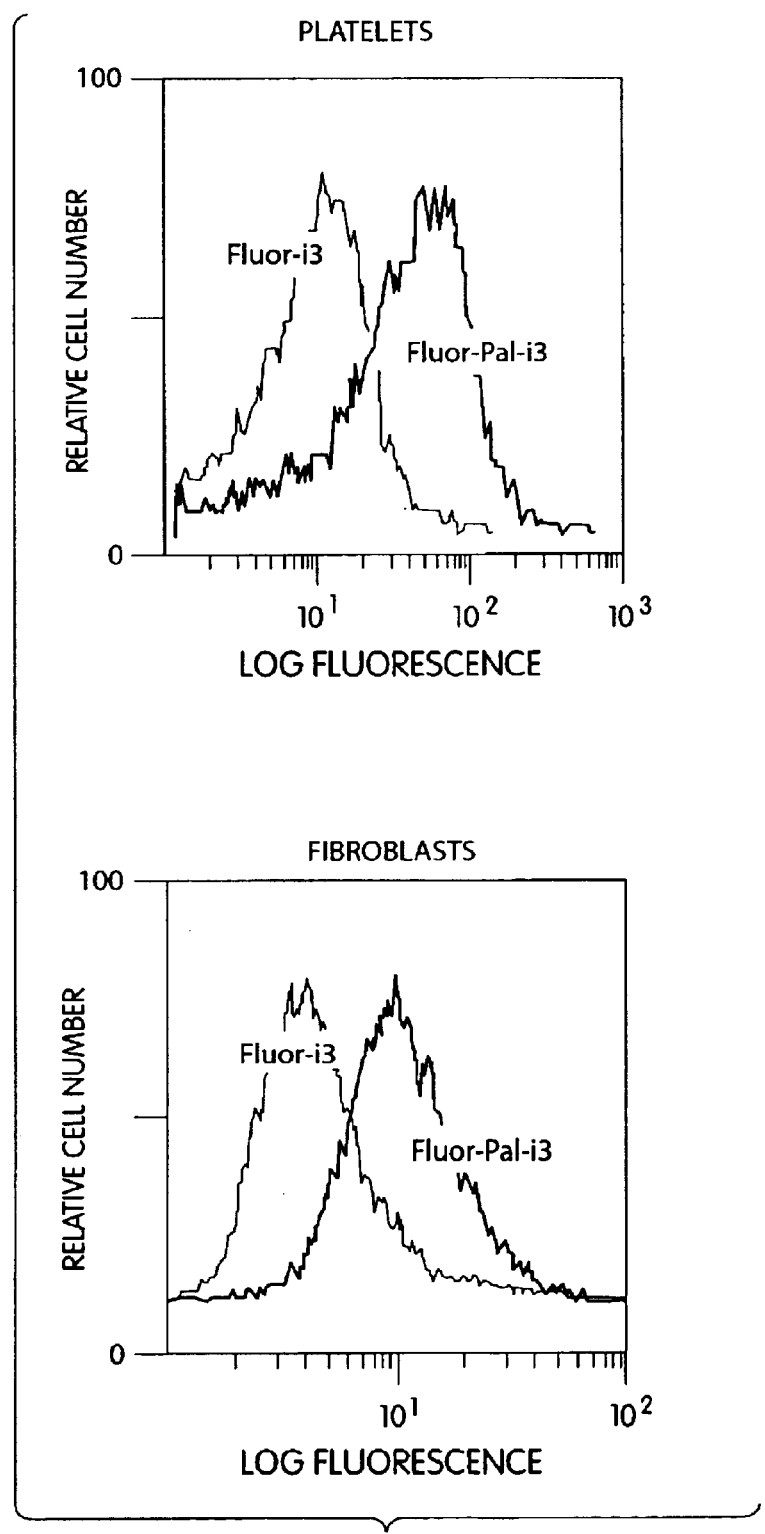

To directly determine whether palmitoylation conferred cell-penetrating abilities, P1-i3-19 and P1pal-19 were labeled with fluorescein (Fluor) and incubated with platelets and PAR1-Rat1 fibroblasts. The cells were then treated with pronase to digest extracellularly bound peptides and analyzed by flow cytometry. Flow cytometry was conducted on platelets or Rat1 fibroblasts stably transfected with PAR1 (K. Ishii et al., *J. Biol. Chem.* 269, 1125–1130 (1994).) that were treated with fluorescein-labeled peptides, Fluor-Pal-i3 (Fluor-P1pal-19) or Fluor-i3 (Fluor-P1-i3-19) as indicated. Fluorescein was conjugated to the i3 peptides by incubating equimolar concentrations of peptide and fluorescein-5-EX-succinimidyl ester (Molecular Probes) for 2 h at 25° C. in DMF/5% triethylamine. The conjugated peptide products were purified from reactants using reverse-phase chromatography. The composition of the conjugated peptides was confirmed by mass spectrometry. Cells were incubated with 10 micromolar Fluor-Pal-i3 or Fluor-i3 for 2 min in PBS/ 0.1% fetal calf serum and then treated with 2 U pronase for 15 min at 37° C. and washed prior to flow cytometry. As shown in FIG. 1E, both platelets and fibroblasts remained strongly fluorescent when treated with Fluor-Pal-i3, as compared to the non-palmitoylated Fluor-i3. Other studies have shown that disruption of the cell membrane abrogates protection against pronase digestion only with Fluor-Pal-i3 and not Fluor-i3, thus confirming that the palmitoylated i3 peptide is membrane permeable.

Example 2

Assessment of the Ability of Pepducins to Activate PAR1 in a Recombinant System

The ability of the pepducins according to the present invention were then assessed for their cell-penetrating ability. Since PAR1 couples to both Gq and Gi(beta/gamma) to stimulate phospholipase C-beta (PLC-beta) (D. T. Hung, T.-K. H. Vu, V. I. Wheaton, K. Ishii, S. R. Coughlin, *J. Clin. Invest.* 89, 1350–1353 (1992).) inositol phosphate (InsP) production in Rat1 fibroblasts expressing human PAR1 (Accumulation of [3H]-inositol phosphates was measured in the presence of 20 mM LiCl. Cells were split into 12 well plates at 200,000 cells/well. [3H]-labeled myoinositol (2 □C.i/mL) was added to cells 24 h prior to the experiment. Wells were rinsed twice with 2 mL DME containing 10 mM HEPES buffer, pH 7.3, then twice with 2 mL PBS containing 20 mM LiCl. Cells were stimulated with agonist or the specified concentrations of i3-loop pepducin for 30 min and then extracted with cold methanol and chloroform. Extracts were loaded onto columns containing 1 mL anion-exchange resin AG1X8, formate form, 100–200 mesh size (Bio-Rad Laboratories, Cambridge, Mass.). After loading, columns were washed twice with 10 mL $H_2O$ and twice with 10 mL 60 mM ammonium formate/5 mM Borax. Column fractions were eluted with 4 mL 2 M ammonium formate/0.1 M formic acid into vials containing 7.5 mL scintillation cocktail and counted. The mean of duplicate or triplicate determinations was expressed as fold-stimulation above non-stimulated cells. The biphasic pepducin data was fit to a two-site equation with one activating site (EC50) and one inhibitory site (IC50)y=(100/(1+(([peptide]/EC50)−n1)))+ (100/(1+(([peptide]/IC50)−n2)))−n3 by non-linear regression analysis using Kaleidagraph 3.05, where n1 and n2 are hill coefficients for the activating and inhibitory phases, respectively, and n3 is the delta maximum amplitude.

PAR1-Rat1 cells or PAR2-COS7 cells were challenged with 1 nM to 10–100 ?M i3 peptide or mastoparan (INLKALAALAKKLL) (SEQ ID NO:25). PLC-beta activity was determined by measuring total [3H]-inositol phosphate (InsP) formation. As shown in FIGS. 2B and C, P1pal-19, and P1pal-13 which lacks the N-terminal six residues of P1pal-19, stimulate InsP production with EC50 values of 180±20 nM and 700±50 nM, respectively, and with similar efficacies as the natural agonist thrombin. In B and C, PLC-? activity was converted to percent of the full response relative to 0.1 nM thrombin (100%) and plotted as a function of peptide concentration using a two-site equation that fit the biphasic activation and inhibition profiles. The full PAR1 thrombin responses for individual experiments were 7.6-fold for P1pal-13, 9.4-fold for P1pal-12 and P1pal-7, 12.4-fold for P1pal-19 and P1pal-19/Rat1 alone, 18-fold for P1pal-19Q, 12.4-fold for P1pal-19E and 9.5-fold for the mastoparan experiment. The minor stimulation of untransfected Rat1 cells (Rat1 alone) by P1pal-19 in C can be attributed to the endogenous rat PAR1 present in these fibroblasts since addition of SFLLRN (SEQ ID NO:24) causes similar stimulation in these untransfected cells (FIG. 2F-'RAT1').

The activation curves of PAR1 are biphasic with a steep activating phase followed by a steep inhibitory phase. Splitting the P1pal-19 agonist into C-terminal P1pal-7 and corresponding N-terminal P1pal-12 peptides results in loss of stimulatory activity in platelets PAR1-Rat1 cells when added separately (FIGS. 1B, 1D, 2B) or together (FIG. 1B). Therefore, in order to have agonist activity, C-terminal PAR1 pepducin residues 301–313 must be contiguous. COS7 cells were transiently transfected with the human receptors PAR1, PAR2, PAR4, cholecystokinin A (CCKA), cholecystokinin B (CCKB), substance P (Sub-P), or rat somatostatin receptor (SSTR2). Transfected cells were challenged with a range of concentrations (0.1–10 micromolar) of P1pal-19, P1pal-13, or P2pal-21 and the highest stimulation of the individual receptors is reported as a black column. The extracellular agonists used to define maximum stimulation for each receptor (open column) were 10 nM thrombin for PAR1, 100 micromolar SLIGKV for PAR2, 100 nM thrombin for PAR4, 300 nM CCK-8 for CCKA and CCKB, 1 micromolar AGCKNFFWKTFTSC (SEQ ID NO:18) for SSTR2, and 1.5 micromolar RPKPQQFFGLM (SEQ ID NO:34) for Sub-P. The full activity profiles for P1pal-19 and P1pal-13 against these receptors are included as supplementary material.

Significantly, neither P1pal-13 nor P1pal-19 stimulate InsP (approximately ÿ11%) in the absence of the PAR1 receptor in COS7 cells (FIGS. 2E, F) or in Rat1 fibroblasts (FIGS. 2C, F). These results demonstrate that activation of G protein signaling by the cell-penetrating peptides requires the presence of receptor. We also showed that positively charged residues in the C-terminal region of the i3 loop peptides previously shown to be essential for activation of G proteins (T. Okamoto et al., Cell 67, 723–730 (1991)) are not necessary for activity of these membrane-tethered agonists. Substitution of the positive charges results in only a 2-fold loss in efficacy of the P1pal-19Q peptide (FIG. 2A) in platelet aggregation (FIG. 1D) or stimulation of InsP in PAR1-Rat1 cells (FIG. 2C). Moreover, the amphipathic wasp venom peptide mastoparan, which is a receptor-independent activator of Gi/o (T. Higashjima, J. Burnier, E. M. Ross, J. Biol. Chem. 265, 14176–14186 (1990)), did not stimulate InsP production in the PAR1-Rat1 cells (FIG. 2C). Thus, the peptides are not simply acting as positively charged amphipathic helixes to activate G protein signaling in an uncontrolled manner. In contrast, mutation of the conserved, more hydrophobic residues in the P1 pal-19E peptide (FIG. 2A) results in ~90% loss of agonist activity (FIGS. 1D, 2C).

Example 3

Specificity of Pepducins for other GPCRs

For these PAR1-derived i3 peptides to be useful as in vivo reagents, it was important to determine the specificity of the peptides for other GPCRs. P1pal-19 and P1pal-13 were tested for agonist activity against an array of six other GPCRs: PAR2, PAR4, cholecystokinin A and B (CCKA and CCKB), somatostatin (SSTR2), and substance P (Sub-P). Of these, PAR2 (S. Nystedt, K. Emilsson, C. Wahlestedt, J. Sundelin, Proc. Natl. Acad. Sci. (USA) 91, 9208–9212 (1994).) is a trypsin/tryptase-activated receptor that is important in inflammation and pain, and PAR4 (W.-F. Xu et al., Proc. Natl. Acad. Sci. (USA) 95, 6642–6646 (1998); M. L. Kahn et al., Nature 394, 690–694 (1998)) is a second thrombin receptor that plays a unique role in platelet aggregation (L. Covic, A. L. Gresser, A. Kuliopulos, Biochemistry 39, 5458–5467 (2000)).

COS7 cells were transiently transfected with each receptor and InsP production measured. P1pal-13 is selective for PAR1 and did not activate the other six GPCRs including PAR2 (FIG. 2E). P1pal-19 can fully activate the highly homologous PAR2 receptor and stimulates CCKB to about 30% of its maximal activity, but does not activate PAR4, CCKA, SSTR2, nor Sub-P (FIG. 2F). These data indicate that the P1pal-13 exhibits complementarity of binding to PAR1 and is highly selective. Inclusion of the six N-terminal amino acids of the i3 loop in P1pal-19 results in less selectivity.

Example 4

Construction of Agonists for GPCRs Other Than PAR1

It was found in some cases that lipidated peptides, based on their corresponding wild-type i3 sequences, were partial agonists with efficacies of 35% for MC4 (FIG. 7), 13% for PAR2 (P2pal-21, FIG. 2D) and 12% for CCKB, and no agonist activity was observed for the i3 peptides of PAR4, SSTR2 and CCKA (Table 1). However, as previously demonstrated, the P1pal-19 PAR1 peptide was able to robustly activate PAR2 (FIG. 2F) indicating that selective mutation of P2pal-21 might create a full agonist for PAR2. An alignment of the i3 loops of PAR1 and PAR2 (FIG. 2A: which shows the alignment of the third intracellular (i3) loops and adjacent transmembrane regions (TM5 and TM6) for PAR1, PAR2 and PAR4 receptors with palmitoylated peptides for PAR1 and PAR2) revealed several sequence differences. Quite strikingly, mutation of the C-terminal Lys to Phe converts the PAR2 peptide, P2pal-21F, into a potent (EC50=25 nM), full agonist of PAR2 with biphasic properties (FIG. 2D. P2pal-21F also activated PAR1 but not PAR4 nor SSTR2 (FIG. 2G). Similar C-terminal Lys/Arg to Phe point mutations of the SSTR2 and CCKA peptides conferred partial agonist activity with their cognate receptors and improved the potency of the CCKB peptide by 15-fold.

These data suggest that the peptide must be tethered or embedded in a lipophilic environment at both termini to exhibit high agonist activity.

Next, to help distinguish between indirect versus direct activation of the G protein by the pepducins, a point mutation was introduced at position S309 located in the C-terminus of the i3 loop/N-terminus of TM6 of PAR1. This perimembranous region has been shown to be important for the fidelity of G pro in coupling for many receptors S. Cotecchia, J. Ostrowski, M. A. Kjelsberg, M. G. Caron, R. J. Lefkowitz, J. Biol. Chem. 267, 1633–1639 (1992). ( )E. Kostenis, B. R. Conklin, J. Wess, Biochemistry 36, 1487–1495 (199); M. A. Kjelsberg, S. Cotecchia, J. Ostrowski, M. G. Caron, R. J. Lefkowitz, J. Biol. Chem. 267, 1430–1433 (1992). and comes into direct contact with the critical DRY residues of TM3 ( )K. Palczewski et al., Science 289, 739–45 (2000). A S309P mutant was constructed and transiently expressed in COS7 cells to the same level as wild type PAR1. COS7 cells were transiently transfected with wild-type (WT), S309P or delta377 PAR1 (A. Kuliopulos et al., Biochemistry 38, 4572–4585 (1999) receptors. Cells were challenged with P1pal-19, SFLLRN (SEQ ID NO:24), or thrombin and PLC-beta activity determined by measuring total [3H]-inositol phosphate formation relative to 100% stimulation (9.6-fold) of WT PAR1 with 0.1 nM thrombin. The apparent inhibition of PAR1 by very high concentrations of thrombin in B is caused by persistent interactions of thrombin to a hirudin-like sequence (K51YEPF55) located in the el exodomain of PAR1 (D. T.

Hung, T.-K. H. Vu, V. I. Wheaton, K. Ishii, S. R. Coughlin, *J. Clin. Invest.* 89, 1350–1353 (1992)). High amounts of thrombin can remain bound to the thrombin-cleaved PAR1 exodomain (S. L. Jacques, M. LeMasurier, P. J. Sheridan, S. K. Seeley, A. Kuliopulos, *J. Biol. Chem.* 275, 40671–40678 (2000)) and inhibit intramolecular liganding by the tethered SFLLRN (SEQ ID NO:24).

Figure 3A:
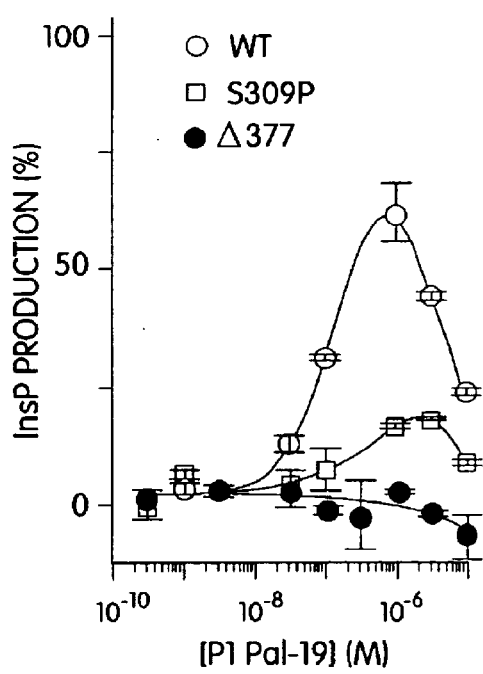
FIGS. 3A through 3C depict the pepducin P1pal-19's inability to activate a C-tail deleted PAR1 and its ability to activate a PAR1 i3-mutant.
Figure 3B:
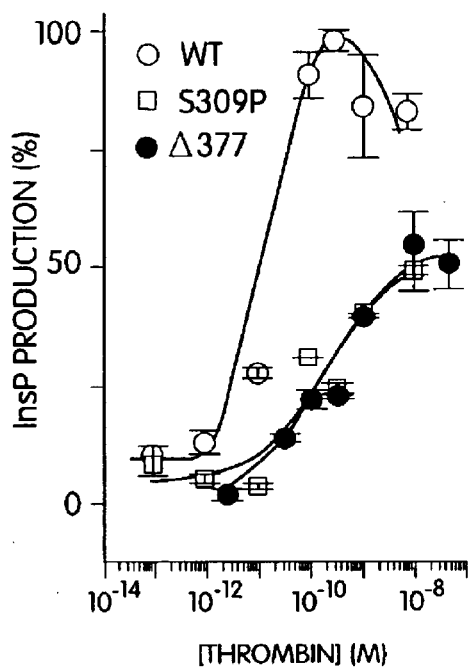

The S309P mutant is deficient in thrombin- and SFLLRN-dependent (SEQ ID NO: 24) stimulation of InsP with 17- and 28-fold loss of potency, and 1.6- and 3.3-fold loss of efficacy, respectively (FIGS. 3B, C). Interestingly, P1pal-19 also stimulates the S309P mutant with parallel losses in potency (13-fold) and efficacy (4.3-fold) relative to its effects on wild type PAR1 (FIG. 3A). Since P1pal-19 did n t correct the signaling defect of the S309P mutation, this indicates that the crucial C-terminal portion of the i3 region in the intact receptor exerts dominant effects in coupling to G protein over that of the exogenous pepducin.

Example 5

Determination of GPCR Regions that Interact with the Pepducins

To define the region(s) of the receptor that might directly contact the i3-pepducin, the entire C-terminal i4 domain of PAR1 was deleted (delta377). The X-ray structure of rhodopsin (K. Palczewski et al., *Science* 289, 739–45 (2000)) indicates that the i3 loop may contact the N-terminal region of alpha-helix 8 and residues to the C-terminal side of the Cys-palmitate moieties within the i4 C-tail. As shown in FIG. 3B and C, the delta377 mutant is defective in stimulating PLC-beta in response to thrombin and SFLLRN (SEQ ID NO:24). Efficacy is reduced by 2–3 fold for the two PAR1 agonists and potency is shifted 22-fold for thrombin and ~30-fold for SFLLRN (SEQ ID NO:24). In contrast, the P1pal-19 pepducin gives effectively no stimulation of PLC-beta in the presence of the delta377 PAR1 mutant (FIG. 3A). These data demonstrate that he C-tail of PAR1 is required for P1pal-19 to activate G-protein and that the C-tail may provide a binding surface for the pepducin agonists.

Example 6

Pepducins that Lack Agonist Activity Still Block GPCR Protein Signaling

Figure 3C:
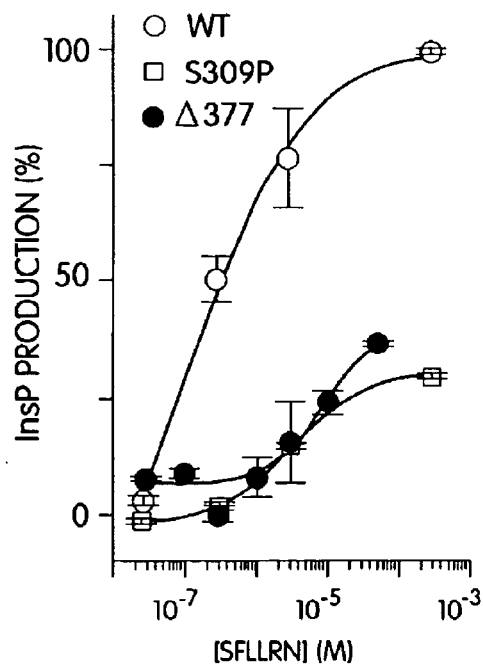
Figure 4A:
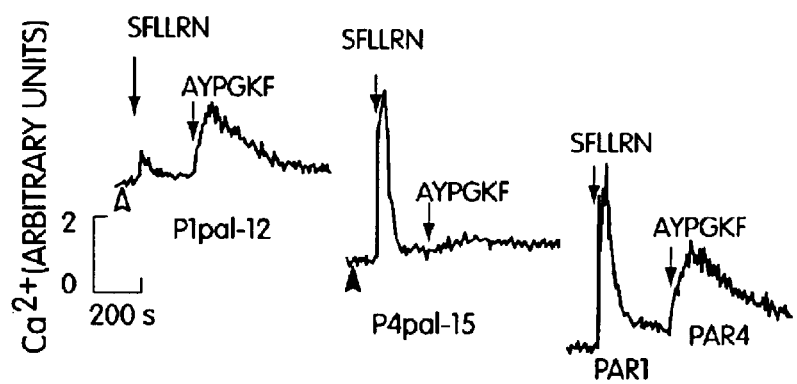
FIGS. 4A through 4E show that the pepducins of the present invention are full antagonists of their cognate receptors.

Human platelets were a convenient, biologically-relevant, system to test the potency and selectivity of anti-PAR1 and anti-PAR4 pepducins since platelets possess both PAR1 and PAR4 thrombin receptors with unique Ca2+ signaling profiles (20). The PAR1 peptide, P1pal12, was found to completely block PAR1 signaling. Platelet Ca2+measurements were performed as in Example 1. Platelets were pre-treated with 3 ?M P1pal-12 (open arrow-head) or P4pal-15 (Pal-HTLAASGRRYGHALR (SEQ ID NO:9); closed arrow-head), and then stimulated with 3 Micromolar SFLLRN (SEQ ID NO:24) or 200 Micromolar AYPGKF (SEQ ID NO:27) as indicated. As shown in FIGS. 4A–C, 3 micromolar P1pal-12 effectively inhibits PAR1 activation of human platelets by SFLLRN (SEQ ID NO:24), but does not block PAR4 activation by AYPGKF (SEQ ID NO:27) (FIG. 4A). Moreover, a pepducin corresponding to the full-length i3 loop of PAR4, P4pal-15, had no agonist activity but was able to fully antagonize PAR4 signaling.

Figure 4B:
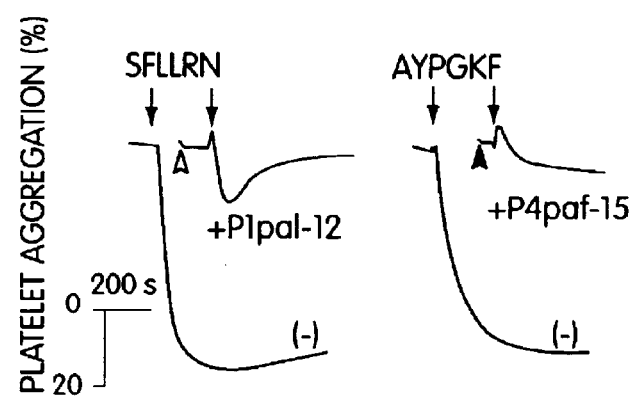
Figure 4C:
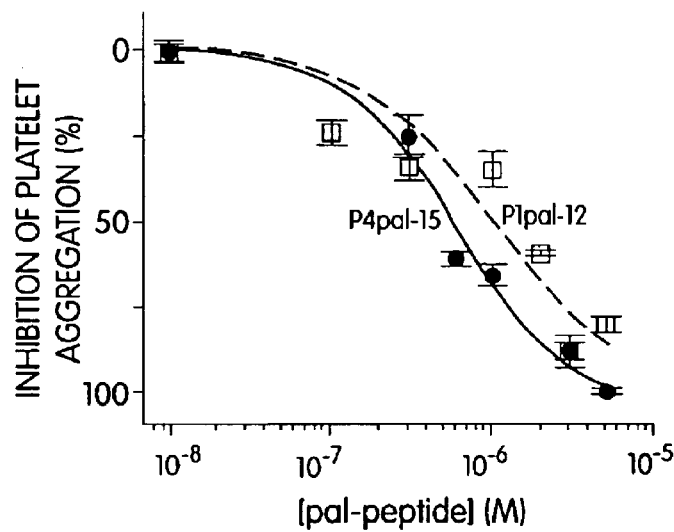

Platelets were then preincubated with either 3 Micromolar P1pal-12 or 3 Micromolar P4pal-15 for 1 min and then challenged with 3 Micromolar SFLLRN (SEQ ID NO:24) or 200 Micromolar AYPGKF (SEQ ID NO:27) and platelet aggregation monitored as in FIG. 1D. Full platelet aggregation traces are also shown for the same amounts of SFLLRN (SEQ ID NO:24) or AYPGKF (SEQ ID NO:27) in the absence (−) of inhibitors. Platelets were pre-treated for 1 min with 0.0 1–5 Micromolar P1pal-12 or P4pal-15 and challenged with 3 Micromolar SFLLRN (SEQ ID NO:24) or 200 Micromolar AYPGKF (SEQ ID NO:27), respectively. As shown in FIG. 4A, 3 micromolar P4pal-15 blocked AYPGKF (SEQ ID NO:27) activation of PAR4 without affecting SFLLRN (SEQ ID NO:24) activation of PAR1 and is an effective inhibitor of platelet aggregation (FIG. 4B, C). Thus, P4pal-15 is the first described high-potency anti-PAR4 compound (IC50=0.6 micromolar in platelets) and is currently being used to help delineate the role of PAR4 in the vascular biology of mice (Covic, Misra, Kuliopulos, (unpublished data).).

Figure 4D:
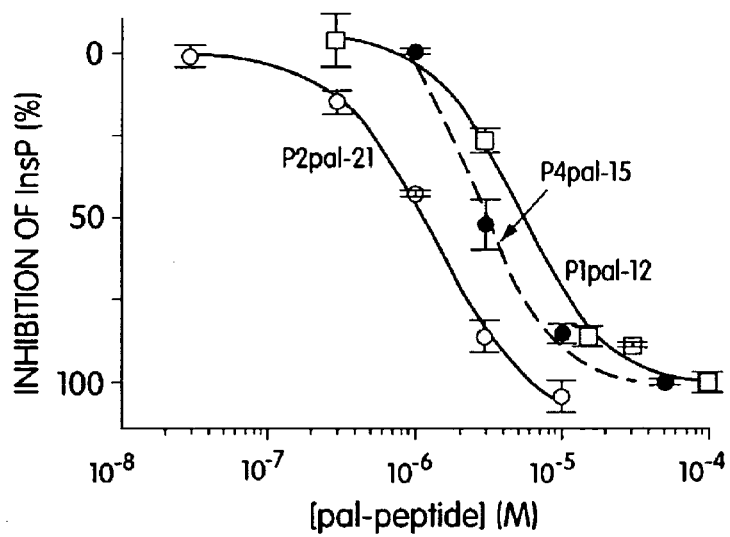
Figure 4E:
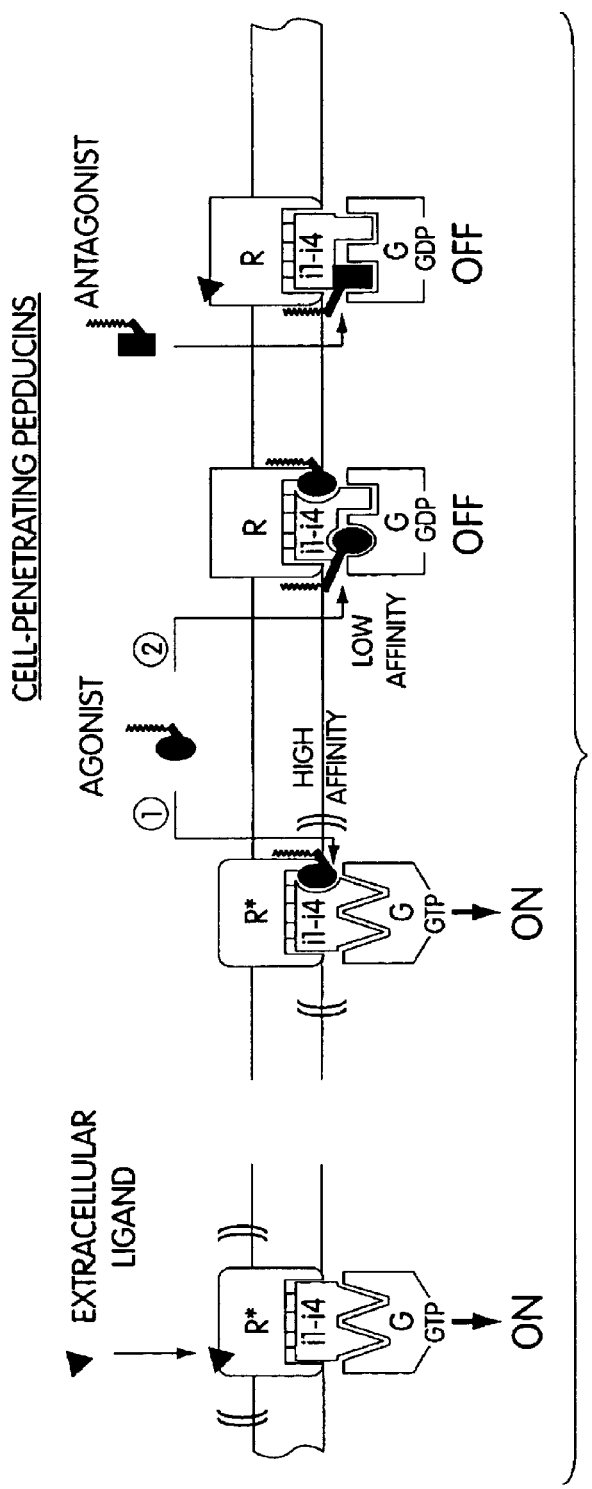
Figure 5:
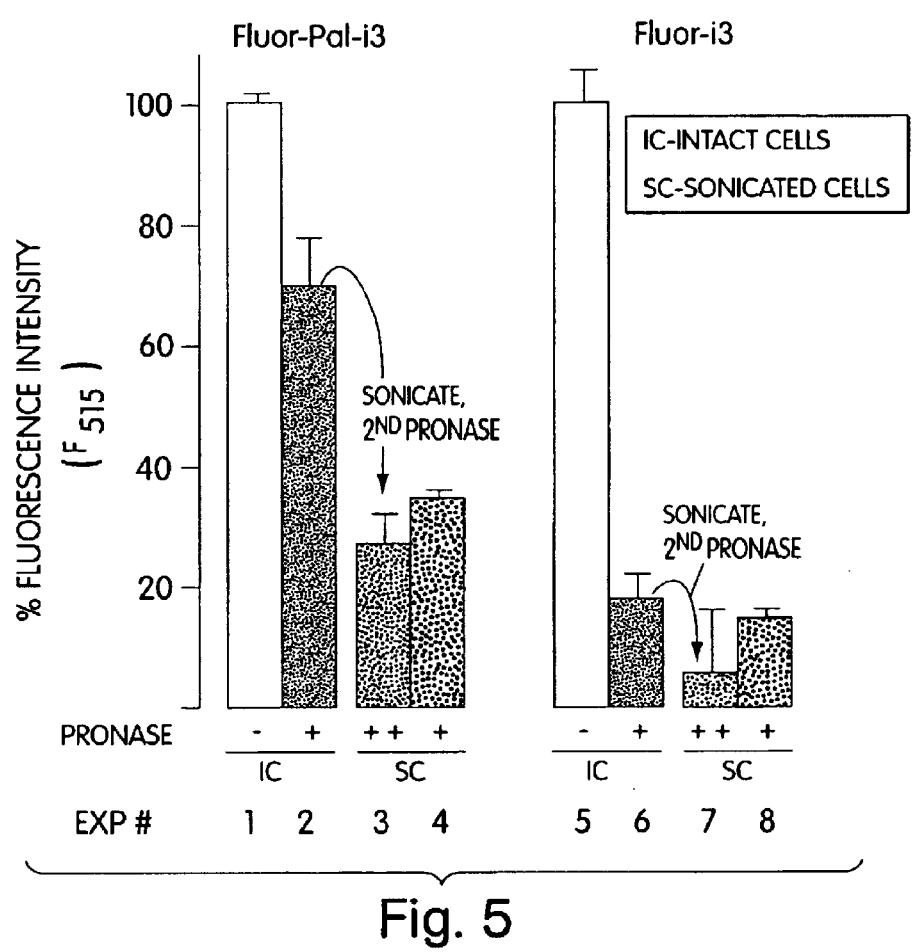
FIG. 5 shows that the peptides of the present invention penetrate intact cells.
Figure 6B:
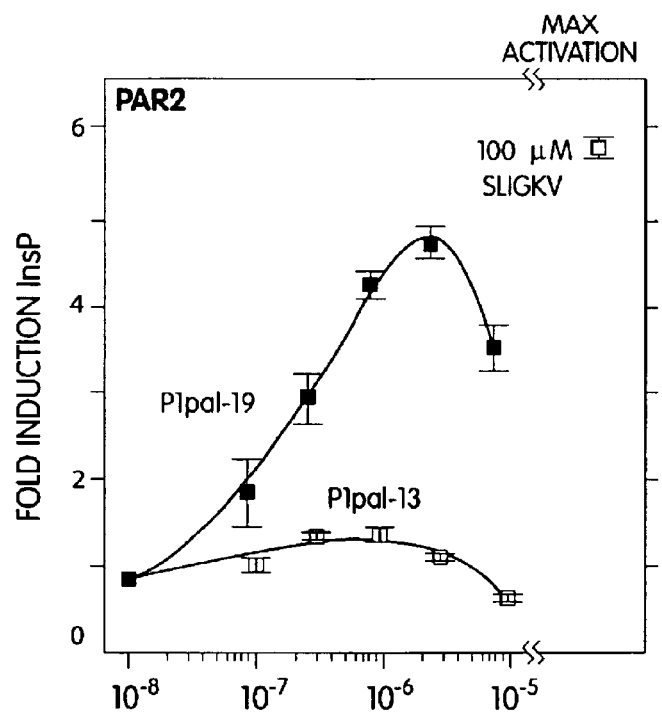
Figure 6C:
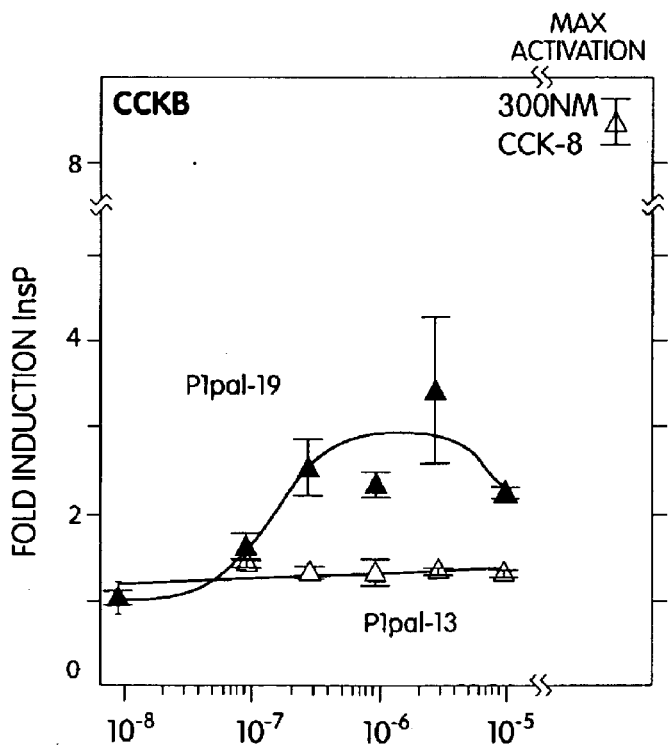
Figure 6D:
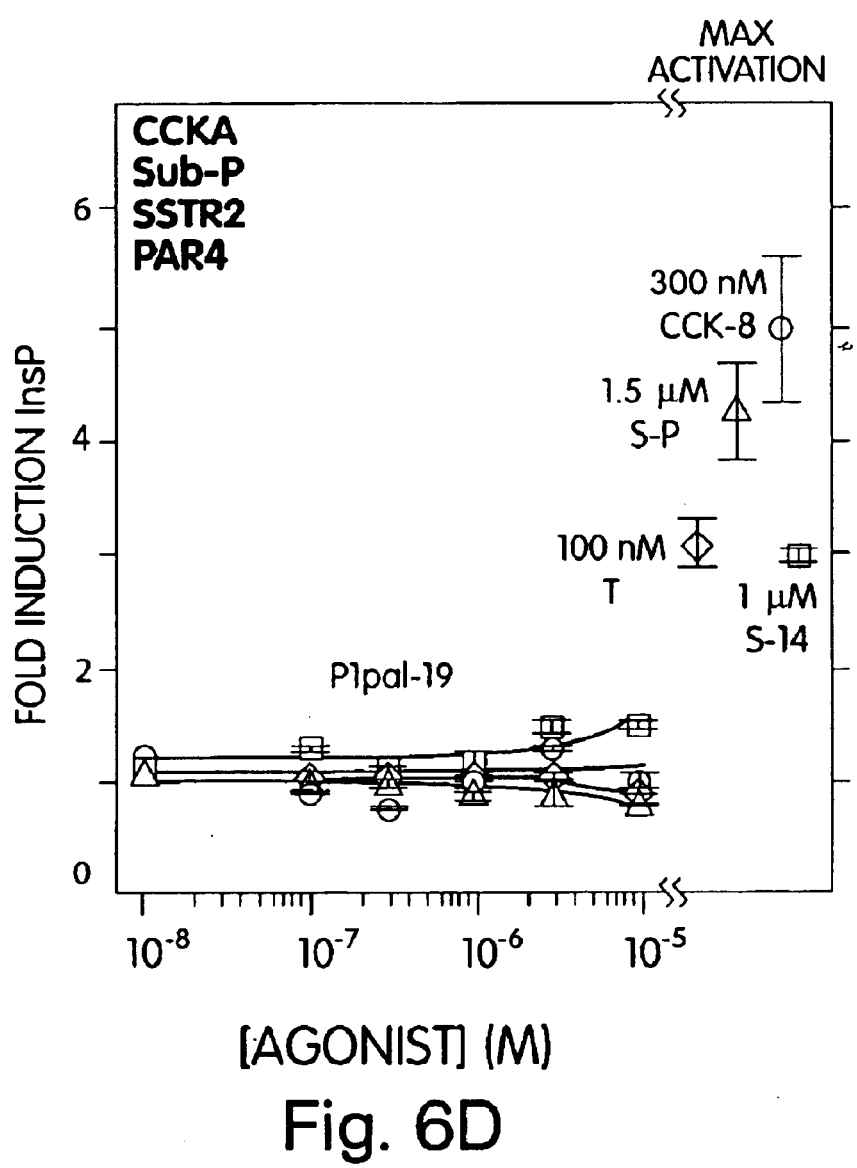

Next, PAR1, PAR4, and PAR2-expressing fibroblasts were pre-treated with 0.03–100 micromolar P1pal-12, P4pal-15, or P2pal-21 for 5 min, and then challenged with extracellular agonists 0.1 nM thrombin, 10 nM thrombin, or 100 micromolar SLIGKV, respectively. Percent InsP inhibition is calculated relative to the full extracellular agonist-stimulated response: 5.2-fold for P1pal-12, 3.1-fold for P4pal-15 and 3.1-fold for P2pal-21. Both anti-PAR1 and anti-PAR4 pepducins are also able to block signaling to PLC-beta in fibroblasts expressing PAR1 or PAR4, respectively (FIG. 4D). Lastly, the PAR2 pepducin, P2pal-21, which is a partial agonist for PAR2 (FIG. 2D), is also able to completely block PAR2 signaling in fibroblasts (FIG. 4D).

Example 7

Ligand Binding Site Peptides with C-terminal Lipid Tethers Interfere with Receptor Liganding Here we describe peptides from the first extracellular domain (e1) PAR1 which have a C-terminal cysteine-lipid for generation of extracellular, membrane-tethered, antagonists of ligand binding to PAR1. In some cases, N-terminal attachment of lipid or hydrophobic tethers to the receptor peptide fragments may lead to loss of activity or may not be optimally placed for targeting the receptor, G protein, or for blocking extracellular liganding. Thus, another embodiment of this technology is attaching lipid tethers to cysteine residues or other derivatizable groups (i.e. —SH, —NH2, —OH) in the receptor fragment that are strategically located at points likely to come into membrane contact. Internal cysteines will be mutated to serine as necessary to avoid spurious derivatization. Based on molecular modeling, some of the peptides will be lipidated at internal, N- and/or C-terminal positions. Glycine (n=1–5) or similar molecular spacers could be placed between sites of lipidation and peptide if necessary for more efficient membrane anchoring or targeting. Dual lipidation may increase effective molarity and reduce entropic contributions at the receptor-effector or receptor-ligand interface.

Figure 8A:
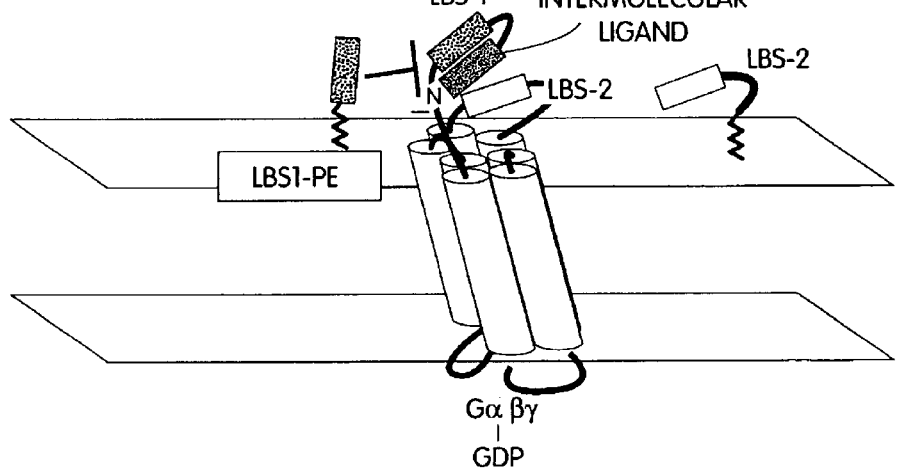
FIG. 8 depicts LBS1 schema.
Figure 8B:
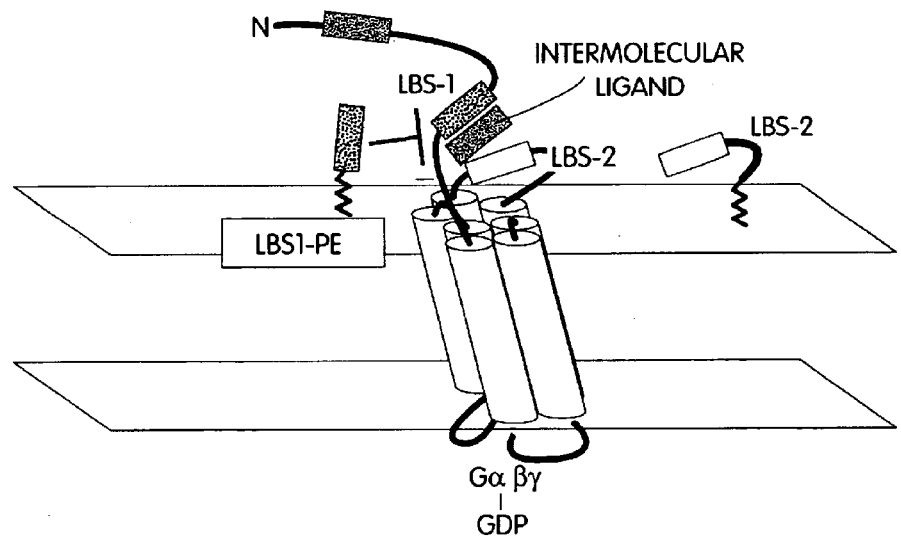

As an example, using NMR structural analysis, we have identified a region on the extracellular surface of PAR1 which forms part of the ligand binding site for PAR1. This region is comprised of receptor residues P85AFIS89 and is termed ligand binding site-1 (LBS-1). Mutation of this region on PAR1 results in severe defects in receptor activation by intermolecular ligand (i.e. SFLLRN (SEQ ID NO:24)) or thrombin. Addition of lipid-tethered peptides that mimic the receptor ligand binding site(s) might be expected to interfere with thrombin-activated receptor (intramolecular ligand) or exogenously added intermolecular ligand (FIG. 8). Other extracellular loops of the receptor also likely make contact with the ligand and could contribute regions termed ligand binding site-2 (LBS-2), LBS-3, etc.

Figure 9C:
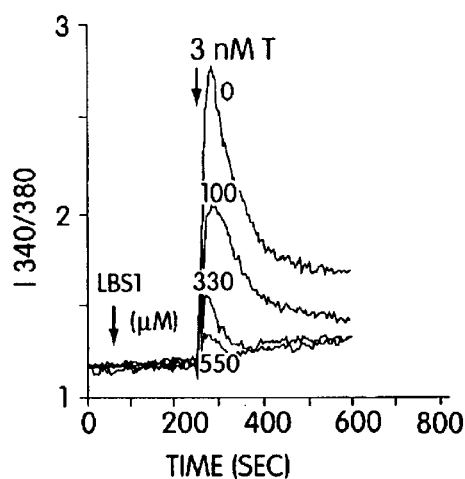
Figure 9D:
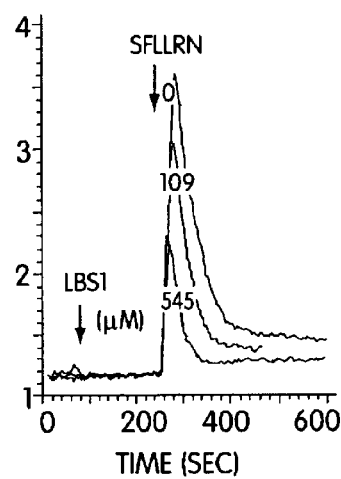
Figure 9E:
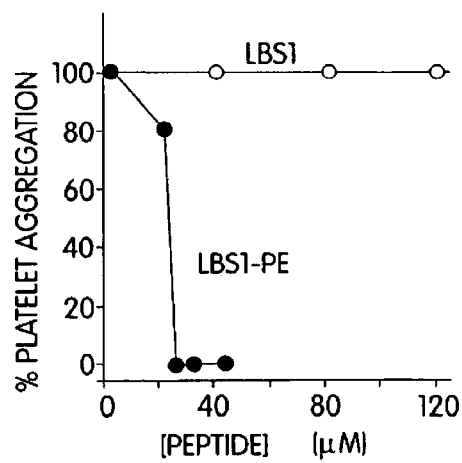

A receptor peptide (LBS1: PAFISEDASGYL-C) (SEQ ID NO:28) was synthesized that contains the P85AFIS89 sequence of PAR1 and adjacent C-terminal residues D90ASGTL95-C that are expected to come into close proximity with the lipid bilayer in the intact receptor (FIG. 9B). The non-lipidated LBS 1 peptide was a relatively poor antagonist against thrombin and SFLLRN (SEQ ID NO:24) activation of PAR1-dependent platelet Ca++ fluxes (FIGS. 9C. and 9D, respectively). Likewise, the non-lipidated LBS1 peptide did not inhibit 3 nM thrombin aggregation of the platelets (FIG. 9E). In marked contrast, the C-terminally lipidated peptide, LBS1-PE (FIG. 9A) was an effective inhibitor of platelet aggregation. As shown in FIG. 9E, 25 micromolar LBS1-PE completely inhibited 3 nM thrombin-induced platelet aggregation.

The LBS1 peptide included a C-terminal cysteine residue and was synthesized by solid-phase fmoc chemistry. Lipidation of the C-terminal cysteine thiol of LBS 1 was done with N-MPB-PE (1,2-dipalmitoyl-sn-glycero-3-phosphoethanolamine-N-[4-(p-maleimidophenyl)-butyramide]) by mixing 2.5 mM peptide and 5 mM N-MPB-PE (Avanti Polar Lipids) in 6% triethylamine/94% dimethylformamide and incubating at ambient temperature (23° C.) for 2 h. The LBS1 peptide-Cys-PE conjugate was purified by Sep-Pak (Waters) C18 reverse-phase chromatography, and identity confirmed by mass spectrometry.

Example 8

Pepducin Activation of the $G_s$-coupled MC4 Obesity Receptor

Figure 7:
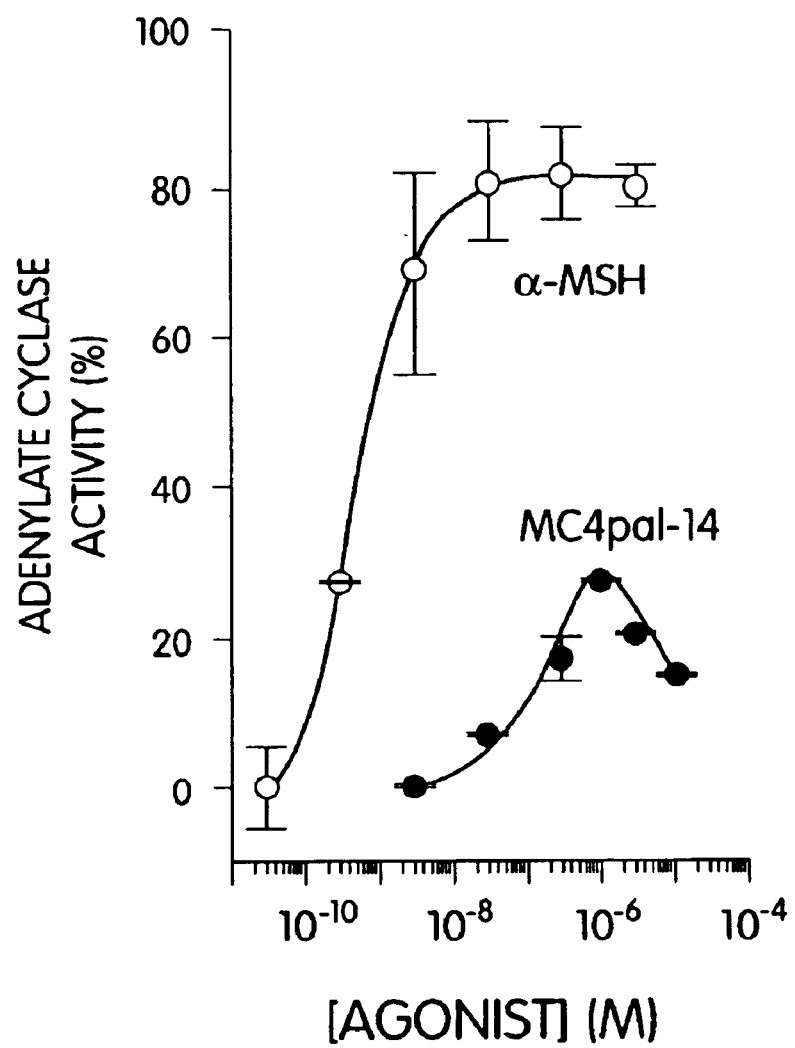
FIG. 7 depicts pepducin activation of the $G_s$-coupled MC4 obesity receptor.

Activation of the MC4 receptor (MC4R) by melanocortin agonists, such as melanocyte stimulating hormone (alpha-MSH) causes anorexia (loss of appetite) and weight loss in mice. Mutations of the MC4R have been found in extremely obese humans. Here, we synthesized a pepducin, MC4pal-14 (Pal- GALRQGANMKGAI) (SEQ ID NO:29) that corresponds to the third intracellular loop of the human MC4R, and tested the pepducin for agonist activity with its cognate receptor. Addition of MC4pal-14 to COS7 fibroblast transiently transfected with MC4R stimulated adenylate cyclase activity by 35% relative to authentic agonist, alpha-MSH. The activity profile of MC4pal-14 is biphasic with an activating phase ($EC_{50}$~150 nM) and inhibitory phase ($IC_{50}$~10 micromolar). These data demonstrate that the pepducins can activate $G_s$-coupled receptor pathways and that MC4pal-14 and its derivatives may have utility as anti-obesity agents in humans. Further, it is noteworthy that unlike systemically injected peptide agonists like alpha-MSH, these cell penetrating pepducins would be expected to cross the blood-brain barrier to activate receptors such as MC4 located in the central nervous system. (FIG. 7).

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

Supplemental Table 1.
Agonist and Antagonist Activity of Pepducins for their Cognate Receptors Expressed in Fibroblast

| Receptor | Pepducin | Sequence | SEQ IN NO | Antagonist $IC_{50}$ ($\mu M$) | $EC_{50}$ ($\mu M$) | Agonist $IC_{50}$ ($\mu M$) | Efficacy (%) |
|---|---|---|---|---|---|---|---|
| PAR1 | P1pal-19 | Pal-RCLSSSAVANRSKKSRALF | 1 | — | 0.18 ± 0.02 | 6.5 ± 1.0 | 90 ± 2 |
|  | P1pal-13 | Pal-AVANRSKKSRALF | 2 | — | 0.70 ± 0.05 | 32 ± 5 | 60–88 |
|  | P1pal-7 | Pal-KKSRALF | 3 | 1.2 ± 0.1 | — | — | — |
|  | P1pal-12 | Pal-RCLSSSAVANRS | 4 | 5.0 ± 1.0 | — | — | — |
|  | P1pal-19Q | Pal-RCLSSSAVANOSQOSQALF | 5 | — | 0.65 ± 0.1 | 30 ± 2 | 46 ± 8 |
|  | P1pal-19E | Pal-RCESSSAEANRSKKERELF | 6 | ≥50 | 2.5 ± 0.5 | 80 ± 5 | 11 ± 1 |
| PAR2 | P2pal-21 | Pal-RMLRSSAMDENSEKKRKRAIK | 7 | 1.0 ± 0.5 | 0.018 ± 0.002 | 1.0 ± 0.2 | 13 ± 2 |
|  | P2pal-21F | Pal-RMLRSSAMDENSEKKRKRAIF | 8 | — | 0.025 ± 0.003 | 7 ± 1 | 95 ± 6 |
| PAR4 | P4pal15 | Pal-HTLAASGRRYGHALR | 9 | 3.0 ± 1.0 | — | — | — |
|  | P4pal15F | Pal-HTLAASGRRYGHALF | 10 | ≥2 | — | — | — |
| SSTR2 | S2pal-23 | Pal-KVKSSGIRVGSSKRKKSEKKVTK | 11 | 2.0 ± 1.0 | — | — | — |
|  | S2pal-23F | Pal-KVKSSGIRVGSSKRKKSEKKVTF | 12 | 3.0 ± 1.0 | 0.1 ± 0.05 | 0.5 ± 0.3 | 15 ± 4 |
| CCKA | Apal-19 | Pal-RIRSNSSAANLMAKKRVIR | 13 | NT | — | — | — |
|  | Apal-19F | Pal-RIRSNSSAANLMAKKRVIEF | 14 | NT | 0.2 ± 0.1 | 2 ± 1 | ≤10 |
| CCKB | Bpal-18 | Pal-SGSRPTQAKLLAKKRVVR | 15 | NT | 1.5 ± 0.5 | 10 ± 2 | 12 ± 3 |
|  | Bpal-18F | Pal-SGSRPTQAKLLAKKRVVF | 16 | NT | 0.10 ± 0.05 | 1.0 ± 0.5 | 13 ± 2 |

Receptor stimulation of PLC-β was determined by measuring total [$^3$H]-inositiol phospate (InsP) formation (15) in Rat1 cells stably expressing PAR1 or in COS7 cells transiently expressing PAR2, PAR4, SSTR2, CCKA, or CCKB.
Antagonist assays were conducted as in FIG. 4D: PAR1, PAR2, PAR4, or SSTR2-expressing cells were pre-treated with their cognate pepducins (10 nM-50 μM) for 5 min, and then stimulated with extracellular agonists 0.1 nM throbin, 100 μM SLIGKV (SEQ ID NO:17), 10 nM thrombin, or 1 μM AGCKNFFWKTFTSC (SEQ ID NO:18), respectively.
In agonist assays, PAR1, PAR2, PAR4, SSTR2, CCKA or CCKB-expressing fibroblast were stumulated with their cognate pepducins (1 nM-50 μM) for 30 min and InsP production measured.
The biphasic pepducin data (see FIG. 2B-D) was fit to a two-site equation, with an $EC_{50}$ for activating phase and $IC_{50}$ for inhibitory phase (15).
Percent efficacy was calculated relative to the full (100%) response to extracellular agonist as above (300 nM CCK-8 for CCKA and CCKB).
NT = not tested.

What is claimed is:

1. A chimeric polypeptide, said chimeric polypeptide comprising:
   a) a first domain consisting essentially of third intracellular loop (i3 loop) or a fragment thereof of a G protein coupled receptor (GPCR), and
   b) a second domain, attached to the first domain, wherein said second domain is a naturally or non-naturally occurring cell-penetrating, membrane-tethering hydrophobic moiety
   wherein said first domain does not comprise a native extracellular portion of said GPCR and wherein said chimeric polypeptide binds to its cognate GPCR.

2. The chimeric polypeptide of claim 1, wherein said hydrophobic moiety is attached at N-terminal end, the C-terminal end, or both the N-terminal and C-terminal ends of said first domain.

3. The chimeric polypeptide of claim 1, wherein said hydrophobic moiety is a lipid.

4. The chimeric polypeptide of claim 3, wherein said hydrophobic moiety is selected from the group consisting of: capryloyl ($C_8$); nonanoyl ($C_9$); capryl ($C_{10}$); undecanoyl ($C_{11}$); lauroyl ($C_2$); tridecanoyl ($C_{13}$); myristoyl ($C_{14}$); pentadecanoyl ($C_{15}$); palmitoyl ($C_{16}$); phtanoyl (($CH_3)_4$); heptadecanoyl ($C_{17}$); and stearoyl ($C_{18}$), wherein said hydrophobic moiety is attached to said chimeric polypeptide with amide bonds, sulfhydryls, amines, alcohols, phenolic groups, or carbon-carbon bonds.

5. The chimeric polypeptide of claim 1, where said i3 loop or fragment thereof comprises at least 3 contiguous amino acid residues of the third intracellular loop.

6. The chimeric polypeptide of claim 1, wherein said is at least 5 i3 loop or fragment thereof comprises at least 5 contiguous amino acid residues of the third intracellular loop.

7. The chimeric polypeptide of claim 1, wherein said i3 loop or fragment thereof comprises at least 7 contiguous amino acid residues of the third intracellular loop.

8. The chimeric polypeptide of claim 1, wherein said first domain comprises a protease-activated receptor (PAR) and said second domain comprises a lipid moiety.

9. The chimeric polypeptide of claim 1, wherein G-protein coupled receptor or fragment thereof, is selected from the group consisting of a luteinizing hormone receptor, a follicle stimulating hormone receptor, a thyroid stimulating hormone receptor, a calcitonin receptor, a glucagon receptor, a glucagon-like peptide 1 receptor (GLP-1), a metabotropic glutamate receptor, a parathyroid hormone receptor, a vasoactive intestinal peptide receptor, a secretin receptor, a growth hormone releasing factor (GRF) receptor, protease-activated receptors (PARs), cholecystokinin receptors, somatostatin receptors, melanocortin receptors, ADP receptors, adenosine receptors, thromboxane receptors, platelet activating factor receptor, adrenergic receptors, 5-HT receptors, CXCR4, CCR5, chemokine receptors, neuropeptide receptors, opioid receptors, parathyroid hormone (PTH) receptor, and vasoactive intestinal peptide (VIP) receptor.

10. A pharmaceutical composition comprising the chimeric polypeptide of claim 1 and a pharmaceutically acceptable carrier.

11. A kit comprising in one or more containers, the pharmaceutical composition of claim 10.

12. The chimeric polypeptide of claim 1, wherein said G-protein coupled receptor is a mammalian G-protein coupled receptor.

13. The chimeric polypeptide of claim 4, wherein said hydrophobic moiety is palmitoyl.

14. The chimeric polypeptide of claim 1, wherein said G-protein coupled receptor is a protease-activated receptor (PAR).

15. The chimeric polypeptide of claim 14, wherein the protease-activated receptor is selected from the group consisting of PAR1, PAR2, and PAR4.

16. The chimeric polypeptide of claim 1, wherein said i3 loop or fragment thereof comprises a sequence selected from the group consisting of SEQ ID NO: 1–16, 19–23, and 29.

17. The chimeric polypeptide of claim 1, wherein said i3 loop or fragment therof comprises a sequence selected from the group consisting of SEQ ID NO: 1–10, and 23.

18. The chimeric polypeptide of claim 1, wherein th said G-protein coupled receptor is selected from the group consisting of CCKA, CCKB, SSTR2, and SubP receptors.

19. The chimeric polypeptide of claim 3, wherein said hydrophobic moiety is a steroid.

20. A chimeric polypeptide, said chimeric polypeptide comprising:
   a) a first domain comprising an isolated i3 loop or fragment thereof of a protease-activated receptor (PAR), and
   b) a second domain, attached to the first domain, wherein said second domain is palmitate.

21. The chimeric polypeptide of claim 1, wherein said hydrophobic moiety is selected from the group consisting of a phospholipid, a steroid, a sphingosine, a ceramide, an octyl-glycine, a 2-cyclohexylalanine, and a benzolylphenylalanine.

22. The chimeric polypeptide of claim 1, further comprising a third domain, said third domain being a cell-penetrating, membrane tethering hydrophobic moiety attached to said first domain.

23. The chimeric polypeptide of claim 1, wherein said i3 loop or fragment thereof comprises the amino acid sequence of SEQ ID NO:1.

24. The chimeric polypeptide of claim 1, wherein said i3 loop or fragment thereof comprises the amino acid sequence of SEQ ID NO:2.

25. The chimeric polypeptide of claim 1, wherein said i3 loop or fragment thereof comprises the amino acid sequence of SEQ ID NO:3.

26. The chimeric polypeptide of claim 1, wherein said i3 loop or fragment thereof comprises the amino acid sequence of SEQ ID NQ:4.

27. The chimeric polypeptide of claim 1, wherein said i3 loop or fragment thereof comprises the amino acid sequence of SEQ ID NO:5.

28. The chimeric polypeptide of claim 1, wherein said i3 loop or fragment thereof comprises the amino acid sequence of SEQ ID NO:6.

29. The chimeric polypeptide of claim 1, wherein said i3 loop or fragment thereof comprises the amino acid sequence of SEQ U) NO:7.

30. The chimeric polypeptide of claim 1, wherein said i3 loop or fragment thereof comprises the amino acid sequence of SEQ ID NO:8.

31. The chimeric polypeptide of claim 1, wherein said i3 loop or fragment thereof comprises the amino acid sequence of SEQ ID NO:9.

32. The chimeric polypeptide of claim 1, wherein said i3 loop or fragment thereof comprises the amino acid sequence of SEQ ID NO:10.

33. The chimeric polypeptide of claim 1, wherein said i3 loop or fragment thereof comprises the amino acid sequence of SEQ ID NO:11.

34. The chimeric polypeptide of claim 1, wherein said i3 loop or fragment thereof comprises the amino acid sequence of SEQ ID NO:12.

35. The chimeric polypeptide of claim 1, wherein said i3 loop or fragment thereof comprises the amino acid sequence of SEQ ID NO:13.

36. The chimeric polypeptide of claim 1, wherein said i3 loop or fragment thereof comprises the amino acid sequence of SEQ ID NO:14.

37. The chimeric polypeptide of claim 1, wherein said i3 loop or fragment thereof comprises the amino acid sequence of SEQ ID NO:15.

38. The chimeric polypeptide of claim 1, wherein said i3 loop or fragment thereof comprises the amino acid sequence of SEQ ID NO:16.

39. The chimeric polypeptide of claim 1, wherein said i3 loop or fragment thereof comprises the amino acid sequence of SEQ ID NO:19.

40. The chimeric polypeptide of claim 1, wherein said i3 loop or fragment thereof comprises the amino acid sequence of SEQ ID NO:20.

41. The chimeric polypeptide of claim 1, wherein said i3 loop or fragment thereof comprises the amino acid sequence of SEQ ID NO:21.

42. The chimeric polypeptide of claim 1, wherein said i3 loop or fragment thereof comprises the amino acid sequence of SEQ ID NO:22.

43. The chimeric polypeptide of claim 1, wherein said i3 loop or fragment thereof comprises the amino acid sequence of SEQ ID NO:23.

44. The chimeric polypeptide of claim 1, wherein said i3 loop or fragment thereof comprises the amino acid sequence of SEQ ID NO:28.

45. The chimeric polypeptide of claim 1, wherein said i3 loop or fragment thereof comprises the amino acid sequence of SEQ ID NO:29.

46. The chimeric polypeptide of claim 1, wherein the hydrophobic moiety is a steroid.

* * * * *

UNITED STATES PATENT AND TRADEMARK OFFICE
CERTIFICATE OF CORRECTION

PATENT NO. : 6,864,229 B2
DATED : March 8, 2005
INVENTOR(S) : Kuliopulos et al.

It is certified that error appears in the above-identified patent and that said Letters Patent is hereby corrected as shown below:

Column 43,
Lines 19-27, should read -- 4. The chimeric polypeptide of claim 3, wherein said hydrophobic moiety is selected from the group consisting of: capryloyl ($C_8$); nonanoyl ($C_9$); capryl ($C_{10}$); undecanoyl ($C_{11}$); lauroyl ($C_{12}$); tridecanoyl ($C_{13}$); myristoyl ($C_{14}$); pentadecanoyl ($C_{15}$); palmitoyl ($C_{16}$); phtanoyl (($CH_3)_4$); heptadecanoyl ($C_{17}$); and stearoyl ($C_{18}$), wherein said hydrophobic moiety is attached to said chimeric polypeptide with amide bonds, sulfhydryls, amines, alcohols, phenolic groups, or carbon-carbon bonds. --.
Lines 31-34, should read -- 6. The chimeric polypeptide of claim 1, wherein said i3 loop or fragment thereof comprises at least 5 contiguous amino acid residues of the third intracellular loop. --.

Column 44,
Lines 50-52, should read -- 29. The chimeric polypeptide of claim 1, wherein said i3 loop or fragment thereof comprises the amino acid sequence of SEQ ID NO:7. --.

Signed and Sealed this

Twenty-seventh Day of September, 2005

JON W. DUDAS
*Director of the United States Patent and Trademark Office*

SEQUENCE LISTING

```
<160> NUMBER OF SEQ ID NOS: 29

<210> SEQ ID NO 1
<211> LENGTH: 19
<212> TYPE: PRT
<213> ORGANISM: Artificial Sequence
<220> FEATURE:
<223> OTHER INFORMATION: Description of Artificial Sequence: Pepducin
      Peptide Sequence

<400> SEQUENCE: 1

Arg Cys Leu Ser Ser Ser Ala Val Ala Asn Arg Ser Lys Lys Ser Arg
  1               5                  10                  15

Ala Leu Phe

<210> SEQ ID NO 2
<211> LENGTH: 13
<212> TYPE: PRT
<213> ORGANISM: Artificial Sequence
<220> FEATURE:
<223> OTHER INFORMATION: Description of Artificial Sequence: Pepducin
      Peptide Sequence

<400> SEQUENCE: 2

Ala Val Ala Asn Arg Ser Lys Lys Ser Arg Ala Leu Phe
  1               5                  10

<210> SEQ ID NO 3
<211> LENGTH: 7
<212> TYPE: PRT
<213> ORGANISM: Artificial Sequence
<220> FEATURE:
<223> OTHER INFORMATION: Description of Artificial Sequence: Pepducin
      Peptide Sequence

<400> SEQUENCE: 3

Lys Lys Ser Arg Ala Leu Phe
  1               5

<210> SEQ ID NO 4
<211> LENGTH: 12
<212> TYPE: PRT
<213> ORGANISM: Artificial Sequence
<220> FEATURE:
<223> OTHER INFORMATION: Description of Artificial Sequence: Pepducin
      Peptide Sequence

<400> SEQUENCE: 4

Arg Cys Leu Ser Ser Ser Ala Val Ala Asn Arg Ser
  1               5                  10

<210> SEQ ID NO 5
<211> LENGTH: 15
<212> TYPE: PRT
<213> ORGANISM: Artificial Sequence
<220> FEATURE:
<223> OTHER INFORMATION: Description of Artificial Sequence: Pepducin
      Peptide Sequence

<400> SEQUENCE: 5

Arg Cys Leu Ser Ser Ser Ala Val Ala Asn Ser Ser Ala Leu Phe
  1               5                  10                  15

<210> SEQ ID NO 6
<211> LENGTH: 19
```

```
<212> TYPE: PRT
<213> ORGANISM: Artificial Sequence
<220> FEATURE:
<223> OTHER INFORMATION: Description of Artificial Sequence: Pepducin
      Peptide Sequence

<400> SEQUENCE: 6

Arg Cys Glu Ser Ser Ser Ala Glu Ala Asn Arg Ser Lys Lys Glu Arg
 1               5                  10                  15

Glu Leu Phe

<210> SEQ ID NO 7
<211> LENGTH: 21
<212> TYPE: PRT
<213> ORGANISM: Artificial Sequence
<220> FEATURE:
<223> OTHER INFORMATION: Description of Artificial Sequence: Pepducin
      Peptide Sequence

<400> SEQUENCE: 7

Arg Met Leu Arg Ser Ser Ala Met Asp Glu Asn Ser Glu Lys Lys Arg
 1               5                  10                  15

Lys Arg Ala Ile Lys
            20

<210> SEQ ID NO 8
<211> LENGTH: 21
<212> TYPE: PRT
<213> ORGANISM: Artificial Sequence
<220> FEATURE:
<223> OTHER INFORMATION: Description of Artificial Sequence: Pepducin
      Peptide Sequence

<400> SEQUENCE: 8

Arg Met Leu Arg Ser Ser Ala Met Asp Glu Asn Ser Glu Lys Lys Arg
 1               5                  10                  15

Lys Arg Ala Ile Phe
            20

<210> SEQ ID NO 9
<211> LENGTH: 15
<212> TYPE: PRT
<213> ORGANISM: Artificial Sequence
<220> FEATURE:
<223> OTHER INFORMATION: Description of Artificial Sequence: Pepducin
      Peptide Sequence

<400> SEQUENCE: 9

His Thr Leu Ala Ala Ser Gly Arg Arg Tyr Gly His Ala Leu Arg
 1               5                  10                  15

<210> SEQ ID NO 10
<211> LENGTH: 15
<212> TYPE: PRT
<213> ORGANISM: Artificial Sequence
<220> FEATURE:
<223> OTHER INFORMATION: Description of Artificial Sequence: Pepducin
      Peptide Sequence

<400> SEQUENCE: 10

His Thr Leu Ala Ala Ser Gly Arg Arg Tyr Gly His Ala Leu Phe
 1               5                  10                  15

<210> SEQ ID NO 11
<211> LENGTH: 23
<212> TYPE: PRT
```

<213> ORGANISM: Artificial Sequence
<220> FEATURE:
<223> OTHER INFORMATION: Description of Artificial Sequence: Pepducin
      Peptide Sequence

<400> SEQUENCE: 11

Lys Val Lys Ser Ser Gly Ile Arg Val Gly Ser Ser Lys Arg Lys
 1               5                  10                  15

Ser Glu Lys Lys Val Thr Lys
            20

<210> SEQ ID NO 12
<211> LENGTH: 23
<212> TYPE: PRT
<213> ORGANISM: Artificial Sequence
<220> FEATURE:
<223> OTHER INFORMATION: Description of Artificial Sequence: Pepducin
      Peptide Sequence

<400> SEQUENCE: 12

Lys Val Arg Ser Ser Gly Ile Arg Val Gly Ser Ser Lys Arg Lys
 1               5                  10                  15

Ser Glu Lys Lys Val Thr Phe
            20

<210> SEQ ID NO 13
<211> LENGTH: 19
<212> TYPE: PRT
<213> ORGANISM: Artificial Sequence
<220> FEATURE:
<223> OTHER INFORMATION: Description of Artificial Sequence: Pepducin
      Peptide Sequence

<400> SEQUENCE: 13

Arg Ile Arg Ser Asn Ser Ser Ala Ala Asn Leu Met Ala Lys Lys Arg
 1               5                  10                  15

Val Ile Arg

<210> SEQ ID NO 14
<211> LENGTH: 20
<212> TYPE: PRT
<213> ORGANISM: Artificial Sequence
<220> FEATURE:
<223> OTHER INFORMATION: Description of Artificial Sequence: Pepducin
      Peptide Sequence

<400> SEQUENCE: 14

Arg Ile Arg Ser Asn Ser Ser Ala Ala Asn Leu Met Ala Lys Lys Arg
 1               5                  10                  15

Val Ile Glu Phe
            20

<210> SEQ ID NO 15
<211> LENGTH: 18
<212> TYPE: PRT
<213> ORGANISM: Artificial Sequence
<220> FEATURE:
<223> OTHER INFORMATION: Description of Artificial Sequence: Pepducin
      Peptide Sequence

<400> SEQUENCE: 15

Ser Gly Ser Arg Pro Thr Gln Ala Lys Leu Leu Ala Lys Lys Arg Val
 1               5                  10                  15

Val Arg

```
<210> SEQ ID NO 16
<211> LENGTH: 18
<212> TYPE: PRT
<213> ORGANISM: Artificial Sequence
<220> FEATURE:
<223> OTHER INFORMATION: Description of Artificial Sequence: Pepducin
      Peptide Sequence

<400> SEQUENCE: 16

Ser Gly Ser Arg Pro Thr Gln Ala Lys Leu Leu Ala Lys Lys Arg Val
 1               5                  10                  15

Val Phe

<210> SEQ ID NO 17
<211> LENGTH: 6
<212> TYPE: PRT
<213> ORGANISM: Artificial Sequence
<220> FEATURE:
<223> OTHER INFORMATION: Description of Artificial Sequence:
      Extracellular Agonist Peptide Sequence

<400> SEQUENCE: 17

Ser Leu Ile Gly Lys Val
 1               5

<210> SEQ ID NO 18
<211> LENGTH: 14
<212> TYPE: PRT
<213> ORGANISM: Artificial Sequence
<220> FEATURE:
<223> OTHER INFORMATION: Description of Artificial Sequence:
      Extracellular Agonist Peptide Sequence

<400> SEQUENCE: 18

Ala Gly Cys Lys Asn Phe Phe Trp Lys Thr Phe Thr Ser Cys
 1               5                  10

<210> SEQ ID NO 19
<211> LENGTH: 89
<212> TYPE: PRT
<213> ORGANISM: Artificial Sequence
<220> FEATURE:
<223> OTHER INFORMATION: Description of Artificial Sequence: Pepducin
      Peptide Sequence

<400> SEQUENCE: 19

Arg Glu Leu Tyr Leu Gly Leu Arg Phe Asp Ser Asp Ser Gln
 1               5                  10                  15

Ser Arg Val Arg Asn Gln Gly Gly Leu Pro Gly Ala Val His Gln Asn
                20                  25                  30

Gly Arg Cys Arg Pro Glu Thr Gly Ala Val Gly Glu Asp Ser Asp Gly
            35                  40                  45

Cys Tyr Val Gln Leu Pro Arg Ser Arg Pro Ala Leu Glu Leu Thr Ala
 50                  55                  60

Leu Thr Ala Pro Gly Pro Gly Ser Gly Ser Arg Pro Thr Gln Ala Lys
 65                  70                  75                  80

Leu Leu Ala Lys Lys Arg Val Val Arg
                85

<210> SEQ ID NO 20
<211> LENGTH: 79
<212> TYPE: PRT
<213> ORGANISM: Artificial Sequence
<220> FEATURE:
```

```
<223> OTHER INFORMATION: Description of Artificial Sequence: Pepducin
      Peptide Sequence

<400> SEQUENCE: 20

Leu Glu Leu Tyr Gln Gly Ile Lys Phe Glu Ala Ser Gln Lys Ser
 1               5                  10                  15

Ala Lys Glu Arg Lys Pro Ser Thr Thr Ser Ser Gly Lys Tyr Glu Asp
                20                  25                  30

Ser Asp Gly Cys Tyr Leu Lys Thr Arg Pro Pro Arg Lys Leu Glu Leu
            35                  40                  45

Arg Gln Leu Ser Thr Gly Ser Ser Ser Arg Ala Asn Arg Ile Arg Ser
     50                  55                  60

Asn Ser Ser Ala Ala Asn Leu Met Ala Lys Lys Arg Val Ile Arg
 65                  70                  75

<210> SEQ ID NO 21
<211> LENGTH: 28
<212> TYPE: PRT
<213> ORGANISM: Artificial Sequence
<220> FEATURE:
<223> OTHER INFORMATION: Description of Artificial Sequence: Pepducin
      Peptide Sequence

<400> SEQUENCE: 21

Ile Thr Leu Trp Ala Ser Glu Ile Pro Gly Asp Ser Ser Asp Arg
 1               5                  10                  15

Tyr His Glu Gln Val Ser Ala Lys Arg Lys Val Val Lys
                20                  25

<210> SEQ ID NO 22
<211> LENGTH: 24
<212> TYPE: PRT
<213> ORGANISM: Artificial Sequence
<220> FEATURE:
<223> OTHER INFORMATION: Description of Artificial Sequence: Pepducin
      Peptide Sequence

<400> SEQUENCE: 22

Lys Val Lys Ser Ser Gly Ile Arg Val Gly Ser Ser Lys Arg Lys
 1               5                  10                  15

Ile Arg Val Gly Ser Ser Lys Arg Arg
                20

<210> SEQ ID NO 23
<211> LENGTH: 12
<212> TYPE: PRT
<213> ORGANISM: Artificial Sequence
<220> FEATURE:
<223> OTHER INFORMATION: Description of Artificial Sequence: Pepducin
      Peptide Sequence

<400> SEQUENCE: 23

Val Ala Asn Arg Ser Lys Lys Ser Arg Ala Leu Phe
 1               5                  10

<210> SEQ ID NO 24
<211> LENGTH: 6
<212> TYPE: PRT
<213> ORGANISM: Artificial Sequence
<220> FEATURE:
<223> OTHER INFORMATION: Description of Artificial Sequence:
      Extracellular PAR1 Ligand Peptide Sequence

<400> SEQUENCE: 24
```

```
Ser Phe Leu Leu Arg Asn
 1               5

<210> SEQ ID NO 25
<211> LENGTH: 14
<212> TYPE: PRT
<213> ORGANISM: Artificial Sequence
<220> FEATURE:
<223> OTHER INFORMATION: Description of Artificial Sequence:
      i3 peptide or mastoparan peptide sequence

<400> SEQUENCE: 25

Ile Asn Leu Lys Ala Leu Ala Ala Leu Ala Lys Lys Ile Leu
 1               5                  10

<210> SEQ ID NO 26
<211> LENGTH: 11
<212> TYPE: PRT
<213> ORGANISM: Artificial Sequence
<220> FEATURE:
<223> OTHER INFORMATION: Description of Artificial Sequence:
      Extracellular Agonist Peptide Sequence

<400> SEQUENCE: 26

Arg Pro Lys Pro Gln Gln Phe Phe Gly Leu Met
 1               5                  10

<210> SEQ ID NO 27
<211> LENGTH: 6
<212> TYPE: PRT
<213> ORGANISM: Artificial Sequence
<220> FEATURE:
<223> OTHER INFORMATION: Description of Artificial Sequence:PAR4 Ligand
      Peptide Sequence

<400> SEQUENCE: 27

Ala Tyr Pro Gly Lys Phe
 1               5

<210> SEQ ID NO 28
<211> LENGTH: 13
<212> TYPE: PRT
<213> ORGANISM: Artificial Sequence
<220> FEATURE:
<223> OTHER INFORMATION: Description of Artificial Sequence: Receptor
      Peptide Sequence

<400> SEQUENCE: 28

Pro Ala Phe Ile Ser Glu Asp Ala Ser Gly Tyr Leu Cys
 1               5                  10

<210> SEQ ID NO 29
<211> LENGTH: 14
<212> TYPE: PRT
<213> ORGANISM: Artificial Sequence
<220> FEATURE:
<223> OTHER INFORMATION: Description of Artificial Sequence: MC4pa1-14
      Pepducin Peptide Sequence

<400> SEQUENCE: 29

Thr Gly Ala Ile Arg Gln Gly Ala Asn Met Lys Gly Ala Ile
 1               5                  10
```